US011519850B2

(12) United States Patent
Meehan

(10) Patent No.: US 11,519,850 B2
(45) Date of Patent: *Dec. 6, 2022

(54) SENSOR CHARACTERIZATION THROUGH FORWARD VOLTAGE MEASUREMENTS

(71) Applicant: Covidien LP, Mansfield, MA (US)

(72) Inventor: Christopher J. Meehan, Denver, CO (US)

(73) Assignee: COVIDIEN LP, Mansfield, MA (US)

( * ) Notice: Subject to any disclaimer, the term of this patent is extended or adjusted under 35 U.S.C. 154(b) by 248 days.

This patent is subject to a terminal disclaimer.

(21) Appl. No.: 17/082,958

(22) Filed: Oct. 28, 2020

(65) Prior Publication Data

US 2021/0333200 A1 Oct. 28, 2021

Related U.S. Application Data

(63) Continuation of application No. 16/857,849, filed on Apr. 24, 2020, now Pat. No. 10,852,230.

(51) Int. Cl.

| | |
|---|---|
| ***A61B 5/1455*** | (2006.01) |
| ***A61B 5/1495*** | (2006.01) |
| ***G01R 19/00*** | (2006.01) |
| ***G01N 21/31*** | (2006.01) |
| ***G01N 21/3504*** | (2014.01) |

(52) U.S. Cl.

CPC ......... *G01N 21/314* (2013.01); *A61B 5/1495* (2013.01); *A61B 5/14552* (2013.01); *G01N 21/3504* (2013.01); *G01R 19/0084* (2013.01); *A61B 2560/0266* (2013.01); *A61B 2562/0238* (2013.01); *G01N 2021/3144* (2013.01); *G01N 2021/3155* (2013.01); *G01N 2021/3181* (2013.01); *G01N 2021/3509* (2013.01)

(58) Field of Classification Search

CPC .............. A61B 5/1455; A61B 5/14551; A61B 5/14552; A61B 5/1495; A61B 2560/0266; A61B 2562/0238

See application file for complete search history.

(56) References Cited

U.S. PATENT DOCUMENTS

| | | | |
|---|---|---|---|
| 5,522,389 | A | 6/1996 | Fischer et al. |
| 6,356,774 | B1 | 3/2002 | Bernstein et al. |
| 7,120,480 | B2 | 10/2006 | Chew et al. |
| 8,515,514 | B2 | 8/2013 | Huiku |
| 9,157,773 | B2 | 10/2015 | Joensuu |
| 9,253,852 | B2 | 2/2016 | Campbell et al. |

(Continued)

OTHER PUBLICATIONS

Prosecution History from U.S. Appl. No. 16/857,849, dated May 4, 2020 through Jul. 28, 2020, 11 pp.

(Continued)

*Primary Examiner* — Eric F Winakur

(74) *Attorney, Agent, or Firm* — Shumaker & Sieffert, P.A.

(57) ABSTRACT

A device for measuring oxygen saturation includes circuitry configured to determine a series resistance for a light emitting diode based on a first diode voltage at the light emitting diode for a first current, a second diode voltage at the light emitting diode for a second current, and a third diode voltage at the light emitting diode for a third current. The circuitry is further configured to determine an intensity of a received photonic signal corresponding to an output photonic signal output using the light emitting diode. The circuitry is further configured to determine an oxygen saturation level based on the intensity of the received photonic signal and the series resistance.

20 Claims, 6 Drawing Sheets

(56) References Cited

U.S. PATENT DOCUMENTS

| | | | |
|---|---|---|---|
| 9,404,961 | B2 | 8/2016 | Gonopolskiy et al. |
| 9,651,632 | B1 | 5/2017 | Knapp et al. |
| 9,839,381 | B1 | 12/2017 | Weber et al. |
| 9,861,317 | B2 | 1/2018 | Ochs |
| 10,123,726 | B2 | 11/2018 | Al-Ali et al. |
| 10,849,538 | B1 | 12/2020 | Meehan et al. |
| 10,852,230 | B1 | 12/2020 | Meehan |
| 2010/0145645 | A1 | 6/2010 | Gonopolskiy et al. |
| 2014/0275890 | A1 | 9/2014 | Meehan et al. |
| 2016/0354017 | A1 | 12/2016 | Meehan et al. |
| 2018/0235525 | A1 | 8/2018 | Blanken |
| 2018/0344227 | A1 | 12/2018 | Cronin et al. |
| 2018/0353111 | A1 | 12/2018 | Buxton et al. |
| 2020/0138349 | A1 | 5/2020 | Lamminmaki et al. |

OTHER PUBLICATIONS

U.S. Appl. No. 17/082,944, filed Oct. 28, 2020, naming inventors Meehan et al.

International Search Report and Written Opinion of International Application No. PCT/US2021/028691, dated Jul. 22, 2021, 14 pp.

SENSOR CHARACTERIZATION THROUGH FORWARD VOLTAGE MEASUREMENTS

CROSS-REFERENCE TO RELATED APPLICATION

This application is a continuation of U.S. patent application Ser. No. 16/857,849 filed Apr. 24, 2020, which is herein incorporated by reference in its entirety.

TECHNICAL FIELD

This disclosure relates to determining blood oxygen saturation with a physiological monitor, and more particularly, relates to determining regional blood oxygen saturation with a regional oximeter or other medical device.

BACKGROUND

An oximeter may output small beams of light through blood and measure an absorption of the small beams of light to estimate oxygen saturation levels in the blood. For example, blood with relatively high oxygenated saturation may absorb more light at a particular wavelength than blood with relatively low oxygenated saturation. As such, the oximeter may determine that oxygenated saturation levels in blood increases as less light at the particular wavelength is received after passing through the blood.

SUMMARY

In general, this disclosure relates to devices, systems, and techniques for determining properties of a sensor device of an oximeter through forward voltage measurements. For example, a device may measure a diode voltage at a light emitting diode while applying different currents at the light emitting diode. The device may determine a resistance for the light emitting diode using the diode voltages. In this example, the device may cancel out the effects of resistance (e.g., from cables, connectors, circuit board traces, etc.) to determine a "true" forward voltage at the light emitting diode to help to ensure proper construction and/or accuracy of the sensor device. For instance, the device may verify, based on the series resistance, a forward voltage, etc., whether the light emitting diode corresponds to a light emitting diode used during calibration. In this way, the device may be validated with calibration values to help to ensure proper construction and/or accuracy of the sensor device. In some examples, the device may verify whether the light emitting diode is operating within a temperature range, account for a shift in wavelength of light emitted by the light emitting diode, and/or use the forward voltage at the light emitting diode to improve other characteristics of the device.

In one example, a device for measuring oxygen saturation includes circuitry configured to: measure a first diode voltage at a light emitting diode while applying a first current through the light emitting diode; measure a second diode voltage at the light emitting diode while applying a second current through the light emitting diode; measure a third diode voltage at the light emitting diode while applying a third current through the light emitting diode; determine a series resistance for the light emitting diode based on the first diode voltage, the second diode voltage, and the third diode voltage; determine an intensity of a received photonic signal corresponding to an output photonic signal output using the light emitting diode; determine an oxygen saturation level based on the intensity of the received photonic signal and the series resistance; and output an indication of the oxygen saturation level.

In another example, a method for measuring oxygen saturation includes: measuring, by circuitry, a first diode voltage at a light emitting diode while applying a first current through the light emitting diode; measuring, by the circuitry, a second diode voltage at the light emitting diode while applying a second current through the light emitting diode; measuring, by the circuitry, a third diode voltage at the light emitting diode while applying a third current through the light emitting diode; determining, by the circuitry, a series resistance for the light emitting diode based on the first diode voltage, the second diode voltage, and the third diode voltage; determining, by the circuitry, an intensity of a received photonic signal corresponding to an output photonic signal output using the light emitting diode; determining, by the circuitry, an oxygen saturation level based on the intensity of the received photonic signal and the series resistance; and outputting, by the circuitry, an indication of the oxygen saturation level.

In one example, a system for measuring oxygen saturation includes: a sensor device comprising a light emitting diode; an oximetry device comprising circuitry configured to: measure a first diode voltage at the light emitting diode while applying a first current through the light emitting diode; measure a second diode voltage at the light emitting diode while applying a second current through the light emitting diode; measure a third diode voltage at the light emitting diode while applying a third current through the light emitting diode; determine a series resistance for the light emitting diode based on the first diode voltage, the second diode voltage, and the third diode voltage; determine an intensity of a received photonic signal corresponding to an output photonic signal output using the light emitting diode; determine an oxygen saturation level based on the intensity of the received photonic signal and the series resistance; and output an indication of the oxygen saturation level.

DETAILED DESCRIPTION

Figure 1:
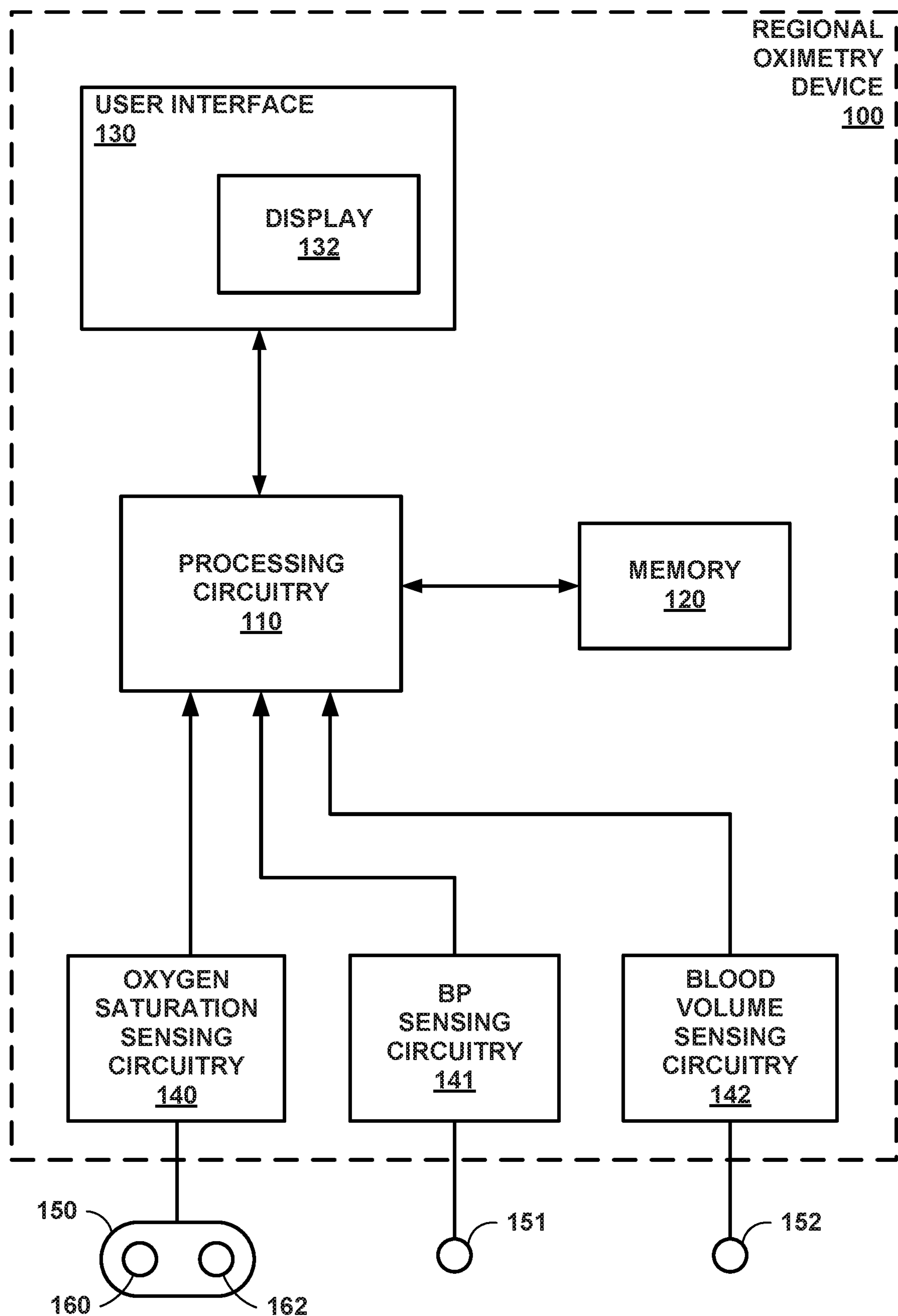
FIG. 1 is a conceptual block diagram illustrating an example regional oximetry device.

An oximeter may refer to a medical device configured to determine an oxygen saturation of an analyzed tissue For purposes of this disclosure an oximeter may be defined as a device that measures other elements besides oxygenation. For example, an oximeter may measure other characteristics and chemical compositions of blood, like carbon monoxide.

In other cases an oximeter may only be used to measure the photoplesmograph of a subject for determination of pulse rate. Examples of an oximeter may include, for example, a pulse oximeter, a regional oximeter, a CO— oximeter, or another oximeter. A pulse oximeter may be configured to estimate oxygen saturation of blood. A regional oximeter may be configured to estimate blood oxygen saturation in a region of a subject's (e.g., a human patient) tissue. For example, the regional oximeter may be configured to determine a differential absorption value for each of two or more wavelengths of light received at two different locations on the subject's body to estimate the regional blood oxygen saturation of hemoglobin in a region of the subject's tissue. For each wavelength of light, the regional oximeter may compare the amount of light absorbed by the subject's tissue in a first region to the amount of light absorbed by the subject's tissue in a second region to derive the differential absorption values. A sensor device may include a regional oximeter and a pulse oximeter.

An oximeter (e.g., a pulse oximeter, a regional oximeter, a CO— oximeter, etc.) may include a sensor device that is placed at a site on a patient, for example, on a fingertip, toe, forehead or earlobe, or in the case of a neonate, across a foot, across a hand, or another location. The oximeter may use a light source to pass light through blood perfused tissue and photoelectrically sense the absorption of the light in the tissue. Additional suitable sensor locations may include, for example, a neck to monitor carotid artery pulsatile flow, a wrist to monitor radial artery pulsatile flow, an inside of a patient's thigh to monitor femoral artery pulsatile flow, an ankle to monitor tibial artery pulsatile flow, around or in front of an ear, the cerebral cortex, locations with strong pulsatile arterial flow, or other locations.

The oximeter may be configured to output a photonic signal that interacts with tissue at one or more wavelengths that are attenuated by the blood in an amount representative of the blood constituent concentration. The oximeter may be configured to generate the photonic signal at red and infrared (IR) wavelengths. The oximeter may estimate the blood oxygen saturation of hemoglobin in arterial blood based on an intensity of the photonic signal at the red wavelength and the photonic signal at the infrared wavelength. While various examples described herein refer to a LED that may output relatively low intensity light, in some examples, LEDs may include devices that output relatively intense beams of light of infrared radiation (e.g., laser diodes), vertical-cavity surface-emitting laser, or another device that emits light using at least one p-type junction and at least one n-type junction. Moreover, while examples described herein may refer to a device emitting light (e.g., LED, laser diode, etc.) similar techniques may be used with devices that receive light (e.g., photodiodes).

Light emitting diodes (LEDs) of an oximeter may have characteristics that impact the wavelength of light emitted. For example, an oximeter may estimate a wavelength of light emitted by a light emitting diode based on a diode voltage measured at the light emitting diode. The diode voltage may include a "true" forward voltage at the light emitting diode and other as voltages resulting from current flowing through a series resistance for the light emitting diode. This series resistance may include resistance from cables, external cables, connectors, traces, and other resistances in series with the light emitting diode. For example, the oximeter may measure the diode voltage across a positive terminal and a negative terminal of the oximeter, where current flows from the positive terminal through one or more cables (e.g., a cable, a cable and an extension cable, etc.) to the light emitting diode and from the light emitting diode through one or more cables to the negative terminal. However, the "true" forward voltage at a light emitting diode may be difficult to accurately measure. For instance, changes in a cable (e.g., from a 6 foot cable to a 10 foot cable) used to connect an oximeter device to a sensor device may significantly change a measured diode voltage, which may result in error in the estimated forward voltage. Moreover, the forward voltage may vary for different currents (see EQUATION 4), which may result in approaches using Ohm's law and assuming a constant true forward voltage being inaccurate. As such, characteristics of the light emitting diode, such as, for example, but not limited to, a temperature at the light emitting diode, a wavelength of light emitted by the light emitting diode, and other characteristic that may be used to verify that LEDs used by the device are accurate and compatible with the device and/or improve a performance of the oximeter may be unavailable to the oximeter.

In accordance with the techniques of the disclosure, a device (e.g., an oximeter) may be configured to account for a series resistance for a light emitting diode. For example, the device may measure a first diode voltage at a light emitting diode that is used to measure oxygen saturation in response to a first current. In this example, the device may measure a second diode voltage at the light emitting diode in response to a second current that has a magnitude of current of twice the first current. Further, the device may measure a third diode voltage at the light emitting diode in response to a third current that has a magnitude of current of twice the second current. The device may estimate a resistance for the light emitting diode using the first diode voltage, the second diode voltage, and the third diode voltage (e.g., using EQUATION 17). In some examples, the device may determine a forward voltage based on a series resistance for the light emitting diode, a first current, and a first diode voltage measured at the light emitting diode in response to the first current (e.g., using EQUATION 24 and/or EQUATION 25).

A device (e.g., an oximeter) may be configured to verify (e.g., validate) that the LEDs used by the device for determining blood oxygen saturation values is of proper construction to conform to the stored calibration information (e.g., are within the range defined by the calibration information). The validation of the LEDs to the calibration information indicates that the LEDs are authenticated and/or verified of proper construction to be used for determining oxygen levels (e.g., measurements should be accurate). In some examples, a valid sensor device may refer to a sensor device that is determined to be of proper construction and/or accuracy. In some examples, a valid sensor device may refer to a sensor device that has characteristics matching or within a range of values for calibration information determined during a calibration of the sensor device. That is, rather than always using calibration information to determine blood oxygen saturation values, a device (e.g., oximeter) may use characteristics of the light emitting diode (e.g., a series resistance, a forward voltage, etc.) and/or of photodiodes to verify that sensor device used by the device corresponds to the calibration information (e.g., satisfy a condition to confirm that the LEDs and/or photodiodes will provide accurate measurements).

For example, the device may determine (e.g. receive, estimate, etc.), during calibration, a forward voltage across the LEDs in response to a single current or in response to each current of multiple currents. In this example, the device may measure a first forward voltage for a first current, a second forward voltage for a second current different (e.g., greater than, less than, etc.) the first current, and so on during calibration. In this example, the device may store the one or more calibrated forward voltages in memory along with calibration information for the LEDs. After calibration, the device may determine the forward voltage using techniques described herein. If the measured forward voltage and the calibrated forward voltage are within a certain tolerance, then the device may determine that the LEDs in service at the device (e.g., an oximeter) are consistent with the calibration information and therefore validated. In response to determining that the LEDs in service at the device are valid, the device may determine, based on the calibration information, an oxygen saturation level using the LEDs. If the measured forward voltage and the calibrated forward voltage are not within the certain tolerance, then the device may determine that the LEDs in service at the device are not consistent with the calibration information, and therefore that the LEDs in service at the device are not validated. In response to determining that the LEDs in service at the device are not validated, the device may refrain from determining an oxygen saturation level. In this way, the device may be validated to be consistent with calibration values to help to ensure proper construction and accuracy of the device.

Additionally, or alternatively, the device may determine (e.g. receive, estimate, etc.), during calibration, a series resistance for a light emitting diode. In this example, the device may store the calibrated series resistance in memory along with calibration information for the LEDs. After calibration, the device may determine the series resistance for the light emitting diode in service using techniques described herein. If the measured series resistance and the calibrated series resistance are within a certain tolerance, then the device may determine that the LEDs in service at the device (e.g., an oximeter) are consistent with the calibration information and therefore validated. In response to determining that the LEDs in service at the device are valid, the device may determine, based on the calibration information, an oxygen saturation level using the LEDs. If the measured series resistance and the calibrated series resistance are not within the certain tolerance, then the device may determine that the LEDs in service at the device are not consistent with the calibration information and therefore that the LEDs in service at the device are not validated. In response to determining that the LEDs in service at the device are not validated, the device may refrain from determining an oxygen saturation level. In this way, the device may be validated to be consistent with calibration values to help to ensure proper construction and accuracy of the device.

The device may use the resistance for the light emitting diode to estimate a temperature of a die for the light emitting diode, which may be used to help to ensure that the sensor device is operating within a target range of operating temperatures. In some examples, the device may apply wavelength compensation to account for a temperature at the die of the light emitting diode, which may improve an accuracy of measurements (e.g., an oxygen saturation level, blood oxygen saturation (SpO2), etc.) performed by the oximetry device.

More specifically, light emitting diodes of a sensor device may be manufactured to output a photonic signal at a particular wavelength with a manufacturing tolerance. For example, a first LED may output a first phonic signal (e.g., red light) at a first wavelength range (e.g., 630 nm-700 nm) with a first manufacturing tolerance of 5%. In this example, a second LED may output a second phonic signal (e.g., infrared light) at a second wavelength range (e.g., 700 nm-1200 nm) with a second manufacturing tolerance of 5%.

To account for the manufacturing tolerances, some oximeters may use calibration information that are established for each sensor. For example, some oximeter may be configured to store calibration information about LEDs of the oximeter in memory (e.g., EEPROM). The calibration information may help to account for manufacturing tolerances of the LEDs, which can shift a wavelength of light emitted by the LEDs. However, changes in temperature may significantly impact a wavelength emitted by a light emitting diode, particularly, light emitting diodes that emit red light, which may shift a few nanometers within an operating range of between 0° C. and 40° C. In accordance with the techniques of the disclosure, a device may estimate a temperature at the light emitting diode based on a forward voltage at the light emitting diode and determine a wavelength of light emitted by a light emitting diode based on the temperature at the light emitting diode. In this way, techniques described herein may account for temperature at light emitting diode, which may improve an accuracy of the oximetry in performing an SpO2 measurement and/or other measurements.

FIG. 1 is a conceptual block diagram illustrating an example regional oximetry device 100. While the example of FIG. 1 describes a regional oximetry device, techniques described herein for accounting for resistance for a light emitting diode may be used in other devices, such as, for example, a pulse oximetry device, a co-oximeter device, or another oximeter device. Regional oximetry device 100 includes processing circuitry 110, memory 120, user interface 130, display 132, sensing circuitry 140, 141, and 142, and sensing device(s) 150, 151, and 152. In some examples, regional oximetry device 100 may be configured to determine and display the cerebral autoregulation status of a patient, e.g., during a medical procedure or for more long-term monitoring, such as monitoring of prenatal infants, children, or adults. A clinician may receive information regarding the cerebral autoregulation status of a patient via display 132 and adjust treatment or therapy to the patient based on the cerebral autoregulation status information. Although regional oximetry device 100 is described as an example device herein, other devices may calculate blood pressure and/or use blood pressure for other physiological monitoring and perform similar a compensation process on blood pressures subjected to abrupt changes in the measured blood pressure values.

Processing circuitry 110 as well as other processors, processing circuitry, controllers, control circuitry, and the like, described herein, may include one or more processors. Processing circuitry 110 may include any combination of integrated circuitry, discrete logic circuity, analog circuitry, such as one or more microprocessors, digital signal processors (DSPs), application specific integrated circuits (ASICs), or field-programmable gate arrays (FPGAs). In some examples, processing circuitry 110 may include multiple components, such as any combination of one or more microprocessors, one or more DSPs, one or more ASICs, or one or more FPGAs, as well as other discrete or integrated logic circuitry, and/or analog circuitry.

Memory 120 may be configured to store measurements of blood pressure, oxygen saturation, blood volume, other physiological parameters, relationships between blood pressure and physiological parameters, MAP values, rSO2 values, COx values, BVS values, HVx values, and/or value(s) of an limit of autoregulation (LLA) and/or a upper limit of autoregulation (ULA), for example. Memory 120 may also be configured to store data such as thresholds for detecting abrupt changes in blood pressure, previous LLA and ULA values, and/or other physiological parameters and expected values of physiological parameters. Memory 120 may also be configured to store data such as threshold levels for physiological parameters, threshold values for blood pressure, and/or threshold levels for signal quality metrics. The thresholds or other data may stay constant throughout the use of device 100 and across multiple patients, or these values may change over time. Memory 120 may store a calibrated values for validating sensing device 150. Examples of calibrated values may include, but are not limited to, one or more forward voltages for a light emitting diode used during calibration, a series resistance for a light emitting diode used during calibration, and/or another value.

Memory 120 may store program instructions, which may include one or more program modules, which are executable by processing circuitry 110. When executed by processing circuitry 110, such program instructions may cause processing circuitry 110 to provide the functionality ascribed to it herein. For example, memory 120 may store instructions regarding how to determine abrupt changes in measured blood pressure, calculating ULA and LLA values, and presenting information to the user via user interface 130. The program instructions may be embodied in software, firmware, and/or RAMware. Memory 120, as well as other memory devices described herein (e.g., memory 220 shown in FIG. 2), may include any volatile, non-volatile, magnetic, optical, circuitry, or electrical media, such as a random access memory (RAM), read-only memory (ROM), non-volatile RAM (NVRAM), electrically-erasable programmable ROM (EEPROM), flash memory, or any other digital media.

User interface 130 and/or display 132 may be configured to present information to a user (e.g., a clinician). User interface 130 and/or display 132 may be configured to present a graphical user interface to a user, where each graphical user interface may include indications of values of one or more physiological parameters of a subject. For example, processing circuitry 110 may be configured to present blood pressure values, other physiological parameter values (e.g., heart rate), and indications of cerebral autoregulation status of a patient via display 132. In some examples, if processing circuitry 110 determines that the cerebral autoregulation status of the patient is impaired, then processing circuitry 110 may present a notification (e.g., an alert) indicating the impaired cerebral autoregulation status via display 132. As another example, processing circuitry 110 may present, via display 132, estimates of regional oxygen saturation (rSO2) for a patient, an estimate of the blood oxygen saturation (SpO2) determined by processing circuitry 110, pulse rate information, respiration rate information, blood pressure, any other patient parameters, or any combination thereof.

User interface 130 and/or display 132 may include a monitor, cathode ray tube display, a flat panel display such as a liquid crystal (LCD) display, a plasma display, or a light emitting diode (LED) display, personal digital assistant, mobile phone, tablet computer, laptop computer, any other suitable display device, or any combination thereof. User interface 130 may also include means for projecting audio to a user, such as speaker(s). Processing circuitry 110 may be configured to present, via user interface 130, a visual, audible, or somatosensory notification (e.g., an alarm signal) indicative of the patient's autoregulation status. User interface 130 may include or be part of any suitable device for conveying such information, including a computer workstation, a server, a desktop, a notebook, a laptop, a handheld computer, a mobile device, or the like. In some examples, processing circuitry 110 and user interface 130 may be part of the same device or supported within one housing (e.g., a computer or monitor).

Sensing circuitry 140, 141, and 142 may be configured to receive physiological signals sensed by respective sensing device(s) 150, 151, and 152 and communicate the physiological signals to processing circuitry 110. Sensing device(s) 150, 151, and 152 may include any sensing hardware configured to sense a physiological parameter of a patient, such as, but not limited to, one or more electrodes, optical receivers, blood pressure cuffs, or the like. Sensing circuitry 140, 141, and 142 may convert the physiological signals to usable signals for processing circuitry 110, such that processing circuitry 110 is configured to receive signals generated by sensing circuitry 140, 141, and 142. Sensing circuitry 140, 141, and 142 may receive signals indicating physiological parameters from a patient, such as, but not limited to, blood pressure, regional oxygen saturation, heart rate, and respiration. Sensing circuitry 140, 141, and 142 may include, but are not limited to, blood pressure sensing circuitry, oxygen saturation sensing circuitry, heart rate sensing circuitry, temperature sensing circuitry, electrocardiography (ECG) sensing circuitry, electroencephalogram (EEG) sensing circuitry, or any combination thereof. In some examples, sensing circuitry 140, 141, and 142 and/or processing circuitry 110 may include signal processing circuitry such as an analog-to-digital converter.

Oxygen saturation sensing device 150 is a regional oxygen saturation sensor configured to generate an oxygen saturation signal indicative of blood oxygen saturation within the venous, arterial, and/or capillary systems within a region of the patient. For example, oxygen saturation sensing device 150 may be configured to be placed on the patient's forehead and may be used to determine the oxygen saturation of the patient's blood within the venous, arterial, and/or capillary systems of a region underlying the patient's forehead (e.g., in the cerebral cortex).

Oxygen saturation sensing device 150 may include emitter 160 and detector 162. Emitter 160 may include at least two light emitting diodes (LEDs), each configured to emit at different wavelengths of light, e.g., red or near infrared light. In some examples, light drive circuitry (e.g., within sensing device 150, sensing circuitry 140, and/or processing circuitry 110) may provide a light drive signal to drive emitter 160 and to cause emitter 160 to emit light. In some examples, the LEDs of emitter 160 emit light in the wavelength range of about 600 nanometers (nm) to about 1000 nm. In a particular example, one LED of emitter 160 is configured to emit light at a wavelength of about 730 nm and the other LED of emitter 160 is configured to emit light at a wavelength of about 810 nm. Other wavelengths of light may also be used in other examples.

Detector 162 may include a first detection element positioned relatively "close" (e.g., proximal) to emitter 160 and a second detection element positioned relatively "far" (e.g., distal) from emitter 160 (these multiple detectors are shown as a single detector in the example of FIG. 1). Light intensity of multiple wavelengths may be received at both the "close" and the "far" detector 162. For example, if two wavelengths are used, the two wavelengths may be contrasted at each location and the resulting signals may be contrasted to arrive at a regional saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). Surface data from the skin and skull may be subtracted out, to generate a regional oxygen saturation signal for the target tissues over time. Oxygen saturation sensing device 150 may provide the regional oxygen saturation signal to processing circuitry 110 or to any other suitable processing device to enable evaluation of the patient's autoregulation status.

Blood pressure sensing device 151 and oxygen saturation sensing device 150 may each be placed on the same or different parts of the patient's body. For example, blood pressure sensing device 151 and oxygen saturation sensing device 150 may physically separate from each other and separately placed on the patient. As another example, blood pressure sensing device 151 and oxygen saturation sensing device 150 may in some cases be part of the same sensor or supported by a single sensor housing. For example, blood pressure sensing device 151 and oxygen saturation sensing device 150 may be part of an integrated oximetry system configured to non-invasively measure blood pressure (e.g., based on time delays in a PPG signal) and regional oxygen saturation. One or both of blood pressure sensing device 151 or oxygen saturation sensing device 150 may be further configured to measure other parameters, such as hemoglobin, respiratory rate, respiratory effort, heart rate, saturation pattern detection, response to stimulus such as bispectral index (BIS) or electromyography (EMG) response to electrical stimulus, or the like. While an example regional oximetry device 100 is shown in FIG. 1, the components illustrated in FIG. 1 are not intended to be limiting. Additional or alternative components and/or implementations may be used in other examples.

Blood pressure sensing device 151 may be any sensor or device configured to obtain the patient's blood pressure (e.g., arterial blood pressure). In one example, the blood pressure sensing device 151 may include or be connected to a probe configured to be inserted into a blood pressure of the patient. In another example, blood pressure sensing device 151 may include a blood pressure cuff for non-invasively monitoring blood pressure or an arterial line for invasively monitoring blood pressure (e.g., a pressure probe configured to be placed within an artery or vein). In certain examples, blood pressure sensing device 151 may include one or more pulse oximetry sensors. In some such cases, the patient's blood pressure may be derived by processing time delays between two or more characteristic points within a single plethysmography (PPG) signal obtained from a single pulse oximetry sensor.

Processing circuitry 110 may be configured to receive one or more physiological signals generated by sensing devices 150, 151, and 152 and sensing circuitry 140, 141, and 142. The physiological signals may include a signal indicating blood pressure, a signal indicating oxygen saturation, and/or a signal indicating blood volume of a patient. Processing circuitry 110 may be configured to determine a relationship between blood pressure values of the patient and a physiological parameter of the patient, such as a correlation index (e.g., COx, a hemoglobin volume index (HVx)), an oxygen saturation value, a blood volume value, a gradient-based metric of two or more physiological parameters, and/or another physiological parameter. Processing circuitry 110 can determine a gradients-based metric by determining respective gradients of signals for physiological parameters and determining whether the respective gradients trend together.

Processing circuitry 110 may be configured to determine the blood pressure values for which the physiological parameter is less than or greater than one or more threshold values. As an example, processing circuitry 110 may determine an estimate of the lower limit of cerebral autoregulation (LLA) based on the lowest blood pressure value at which the expected value of COx is less than a threshold value, such as 0.5, 0.4, 0.3, 0.2, 0.1, or 0.0 (e.g., wherein 1.0 represents full correlation and 0.0 represents no correlation between blood pressure and rSO2). Thus, processing circuitry 110 may determine estimates of the limits of cerebral autoregulation (e.g., the LLA and the ULA) based on the blood pressure and rSO2.

A forward voltage at a diode (e.g., a light emitting diode) may vary for different currents (e.g., see EQUATION 4) in a non-linear manner, which may result in error in techniques relying on a constant forward voltage or a forward voltage that is linearly dependent on current through the diode. For example, a second diode voltage measured when applying a second current through a diode may not be equal to twice a first diode voltage when applying a first current through the diode that is half a magnitude of the second current. As described further below, diodes may generate a forward voltage in response to an electrical current based on multiple factors, such as, for example, a temperature at the light emitting diode, one or more device dependent constants, and current flowing through the diode. Moreover, a forward voltage at a diode may not be linearly proportional to a current flowing through the diode. For instance, the forward voltage at a diode may have a rate of change proportional to a natural logarithm of current flowing through the diode.

In accordance with the techniques of the disclosure, a device such as regional oximetry device 100 may include voltage measuring circuitry (e.g., within sensing device 150, sensing circuitry 140, and/or processing circuitry 110) that is configured to measure a first diode voltage at a light emitting diode (e.g., a red diode, an infrared diode, etc.) of emitter 160 while applying a first current through the light emitting diode. Similarly, the voltage measuring circuitry may measure a second diode voltage at the light emitting diode while applying a second current through the light emitting diode and measure a third diode voltage at the light emitting diode while applying a third current through the light emitting diode. For example, the voltage measuring circuitry may apply the first current at a first magnitude of current, apply the second current at a second magnitude of current that corresponds to the first magnitude of current multiplied by a multiplication factor (e.g., 2, 3, 4, etc.) and apply the third current at a third magnitude of current that corresponds to the second magnitude of current multiplied by the multiplication factor. In this way, a difference between the first current and the second current and/or a difference between the second current and the third current may result in a "constant" forward voltage at the light emitting diode because of how a forward voltage at the diode changes in response to the doubling, tripling, quadrupling, etc. of current at the light emitting diode (e.g., see EQUATION 8).

Processing circuitry 110 may determine a series resistance for the light emitting diode based on the first diode voltage, the second diode voltage, and the third diode voltage. In some examples, processing circuitry 110 may determine the series resistance based on the first diode voltage, the second diode voltage, the third diode voltage, and at least one of the magnitude of the first current, the magnitude of the second current, and the magnitude of the third current. For example, processing circuitry 110 may subtract the second diode voltage from the first diode voltage to determine a first diode difference value, subtract the third diode voltage from the second diode voltage to determine a second diode difference value, and divide a result of subtracting the first diode difference value from the second diode difference value by a magnitude of the first current to generate the series resistance for the light emitting diode. In this way, techniques described herein may determine a forward voltage at a light emitting diode in a manner that accounts for device specific parameters of the light emitting diode and/or a non-linear forward voltage relationship between forward voltage and current at the light emitting diode.

Processing circuitry 110 may be configured to verify (e.g., validate) that the LEDs used by the device for determining blood oxygen saturation values conform to the stored calibration information (e.g., are within the range defined by the calibration information). The validation of the LEDs to the calibration information may indicate that the LEDs are verified to be used for determining oxygen levels (e.g., measurements should be accurate). For example, processing circuitry 110 may determine that a light emitting diode is valid in response to determining that the estimated series resistance for the light emitting diode corresponds to (e.g., matches) the calibrated series resistance for calibration information that was determined (e.g., measured or calculated) during calibration.

Processing circuitry 110 may determine that a light emitting diode is valid in response to determining that a forward voltage for the light emitting diode corresponds to (e.g., matches) a calibrated forward voltage for calibration information that was determined (e.g., measured or calculated) during calibration. For example, processing circuitry 110 may determine a forward voltage based on a series resistance for the light emitting diode, a first current, and a first diode voltage measured at the light emitting diode in response to the first current (e.g., using EQUATION 24 and/or EQUATION 25). In this example, processing circuitry 110 may determine that the light emitting diode is valid when the forward voltage for the light emitting diode corresponds to (e.g., matches) the calibrated forward voltage for calibration information that was determined (e.g., measured or calculated) during calibration.

Processing circuitry 110 may, in response to determining that one or more light emitting diodes and/or one or more photodiodes are valid, determine an intensity of a received photonic signal corresponding to an output photonic signal output using the light emitting diode. For example, processing circuitry 110 may drive the light emitting diode to output the output photonic signal towards a subject's tissue and receive, from a detector (e.g., one or more photodiodes), the received photonic signal after the output photonic signal transmits through the subject's tissue.

Processing circuitry 110 may determine an oxygen saturation level based on the intensity of the received photonic signal and the series resistance. For example, processing circuitry 110 may determine a temperature at the light emitting diode based on the series resistance, the first diode voltage, and the second diode voltage. More specifically, processing circuitry 110 may subtract the second diode voltage from the first diode voltage to determine a first diode difference value, subtract a result of multiplying a magnitude of the first current and the series resistance from the first diode difference value to generate a voltage value for the light emitting diode, and multiply the voltage value for the light emitting diode and a factor parameter value for the light emitting diode to determine the temperature at the light emitting diode.

Processing circuitry 110 may estimate a wavelength for a output photonic signal based on the temperature at the light emitting diode. For example, processing circuitry 110 may determine the oxygen saturation level based on the estimated wavelength for the output photonic signal and the intensity of the received photonic signal and the series resistance.

In the above examples, processing circuitry 110, light drive circuitry, and voltage measuring circuitry are described as performing the example techniques, wherein light drive circuitry and voltage measurement circuitry may be part of processing circuitry 110, sensing device 150 and/or sensing circuitry 140). However, any one or combination of processing circuitry 110, sensing circuitry 140, and/or sensing device 150 may be configured to perform the example techniques. For instance, the example techniques may be performed by circuitry, and example of the circuitry includes any one or any combination of processing circuitry 110, sensing circuitry 140, and/or sensing device 150.

Figure 2:
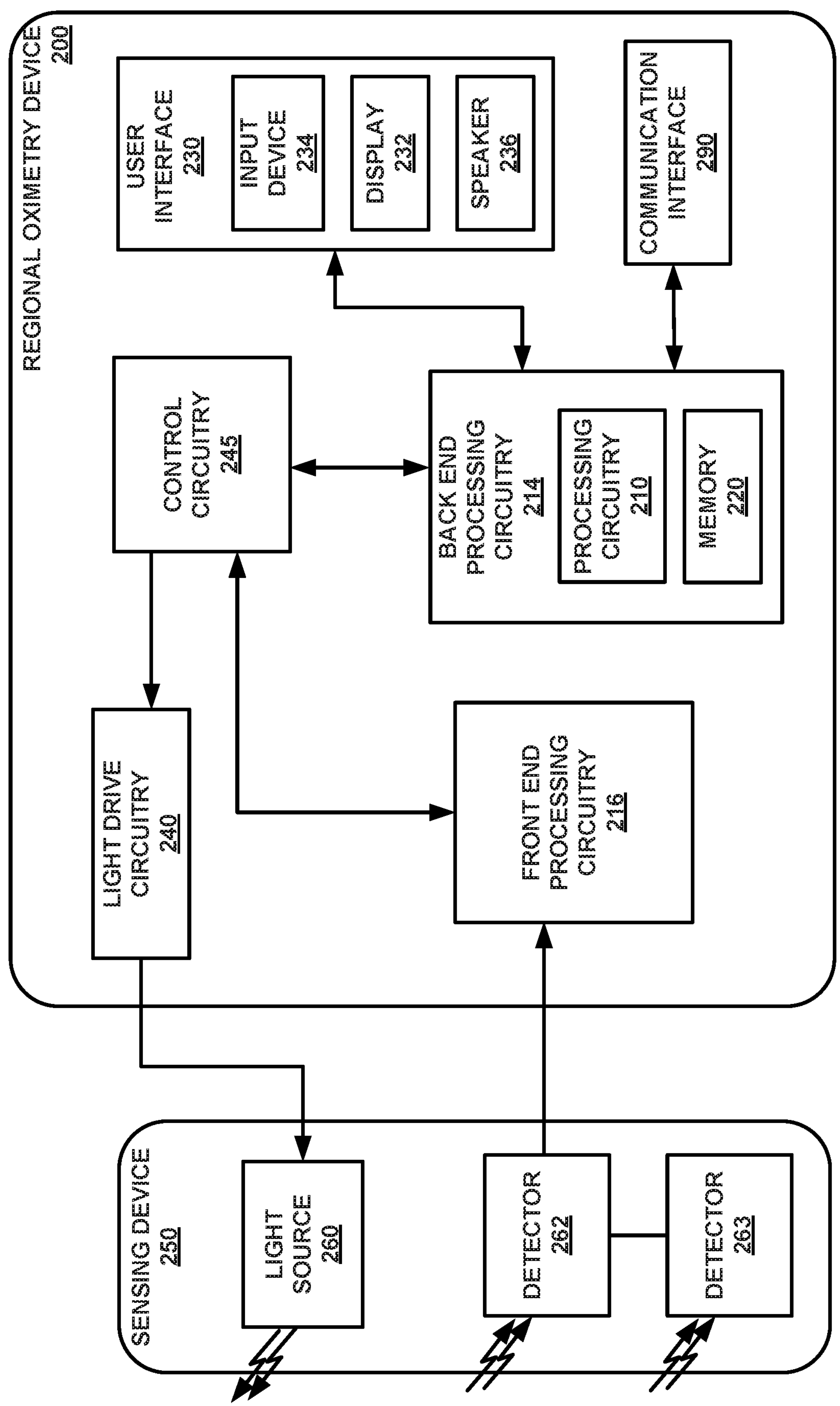
FIG. 2 is a conceptual block diagram illustrating an example regional oximetry device configured to monitor an autoregulation status of a patient.

FIG. 2 is a conceptual block diagram illustrating an example regional oximetry device 200 configured to monitor the autoregulation status of a patient. While the example of FIG. 2 describes a regional oximetry device, techniques described herein for validating light emitting diodes may be used in other devices, such as, for example, a pulse oximetry device. In the example shown in FIG. 2, regional oximetry device 200 is coupled to sensing device 250 and may be collectively referred to as a regional oximetry system, which each generate and process physiological signals of a subject. In some examples, sensing device 250 and regional oximetry device 200 may be part of an oximeter. Regional oximetry device 200 and sensing device 250 may be examples of regional oximetry device 100 and sensing device 150, respectively, of FIG. 1. As shown in FIG. 2, regional oximetry device 200 includes back-end processing circuitry 214, user interface 230, light drive circuitry 240, front-end processing circuitry 216, control circuitry 245, and communication interface 290. Regional oximetry device 200 may be communicatively coupled to sensing device 250. Regional oximetry device 200 is an example of regional oximetry device 100 shown in FIG. 1. In some examples, regional oximetry device 200 may also include a blood pressure sensor and/or a blood volume sensor (e.g., sensing devices 151 and 152 of FIG. 1).

In the example shown in FIG. 2, sensing device 250 includes light source 260, detector 262, and detector 263. Light source 260 may be an example of light source 160 of FIG. 1. Detectors 262 and 263 may be examples of detector 162 of FIG. 1. In some examples, sensing device 250 may include more than two detectors. Light source 260 may be configured to emit photonic signals having two or more wavelengths (e.g., up to four or more wavelengths, more than 4 wavelengths, etc.) of light (e.g., red and infrared (IR), or another wavelength of light) into a subject's tissue. For example, light source 260 may include a red light emitting light source and an IR light emitting light source, (e.g., red and IR LEDs), for emitting light into the tissue of a subject to generate physiological signals. In some examples, the red wavelength may be between about 600 nm and about 700 nm, and the IR wavelength may be between about 800 nm and about 1000 nm. Other wavelengths of light may be used in other examples. Light source 260 may include any number of light sources with any suitable characteristics. In examples in which an array of sensors is used in place of sensing device 250, each sensing device may be configured to emit a single wavelength. For example, a first sensing device may emit only a red light while a second sensing device may emit only an IR light. In some examples, light source 260 may be configured to emit two or more wavelengths of near-infrared light (e.g., wavelengths between 600 nm and 1000 nm) into a subject's tissue. In some examples, light source 260 may be configured to emit four wavelengths of light (e.g., 724 nm, 770 nm, 810 nm, and 850 nm) into a subject's tissue. In some examples, the subject may be a medical patient.

As used herein, the term "light" may refer to energy produced by radiative sources and may include one or more of ultrasound, radio, microwave, millimeter wave, infrared, visible, ultraviolet, gamma ray or X-ray electromagnetic radiation. Light may also include any wavelength within the radio, microwave, infrared, visible, ultraviolet, or X-ray spectra, and that any suitable wavelength of electromagnetic radiation may be appropriate for use with the present techniques. Detectors 262 and 263 may be chosen to be specifically sensitive to the chosen targeted energy spectrum of light source 260.

Detectors 262 and 263 may be configured to detect the intensity of multiple wavelengths of near-infrared light. In some examples, detectors 262 and 263 may be configured to detect the intensity of light at the red and IR wavelengths. In some examples, an array of detectors may be used and each detector in the array may be configured to detect an intensity of a single wavelength. In operation, light may enter detector 262 after passing through the subject's tissue, including skin, bone, and other shallow tissue (e.g., non-cerebral tissue and shallow cerebral tissue). Light may enter detector 263 after passing through the subject's tissue, including skin, bone, other shallow tissue (e.g., non-cerebral tissue and shallow cerebral tissue), and deep tissue (e.g., deep cerebral tissue). Detectors 262 and 263 may convert the intensity of the received light into an electrical signal. The light intensity may be directly related to the absorbance and/or reflectance of light in the tissue. That is, when more light at a certain wavelength is absorbed or reflected, less light of that wavelength is received from the tissue by detectors 262 and 263.

Detectors 262 and/or detector 263 may determine a first intensity of a first received photonic signal corresponding to a first output photonic signal (e.g., red light) output using a light emitting diode of light source 260. More specifically, processing circuitry (e.g., light drive circuitry 240) may be configured to drive the light emitting diode of light source 260 to output the output photonic signal towards a subject's tissue and receive, from detector 262 and/or detector 263, the first received photonic signal after the output photonic signal transmits through the subject's tissue.

After converting the received light to an electrical signal, detectors 262 and 263 may send the detection signals to regional oximetry device 200, which may process the detection signals and determine physiological parameters (e.g., based on the absorption of the red and IR wavelengths in the subject's tissue at both detectors). For example, regional oximetry device 200 may determine an oxygen saturation level based on the intensity of the received photonic signal. More specifically, processing circuitry 210 may estimate a wavelength for the output photonic signal based a temperature at a light emitting diode (e.g., a red light emitting diode, an infrared light emitting diode, etc.). For instance, processing circuitry 210 may estimate the wavelength for the output photonic signal as equal to a wavelength identified in calibration information stored in memory 220 that corresponds to the temperature at the light emitting diode.

Processing circuitry 210 may determine the oxygen saturation level based on the wavelength for the output photonic signal and the intensity of the received photonic signal. For example, processing circuitry 210 may determine the oxygen saturation level by matching an amount of absorption of light at a particular wavelength (e.g., a difference in magnitude between an emitted light and a received light) with a table entry stored in memory 220 and outputting a corresponding oxygen saturation level for the absorption of light at the particular wavelength. For instance, processing circuitry 210 may determine the oxygen saturation level by matching a first amount of absorption of light at a first wavelength (e.g., red light) and a second amount of absorption of light at a second wavelength (e.g., infrared light) with a table entry stored in memory 220 and outputting a corresponding oxygen saturation level.

One or more of the detection signals may be preprocessed by sensing device 250 before being transmitted to regional oximetry device 200. Additional example details of determining oxygen saturation based on light signals may be found in commonly assigned U.S. Pat. No. 9,861,317, which issued on Jan. 9, 2018, and is entitled "Methods and Systems for Determining Regional Blood Oxygen Saturation," the entire content of which is incorporated herein by reference.

Control circuitry 245 may be coupled to light drive circuitry 240, front-end processing circuitry 216, and back-end processing circuitry 214, and may be configured to control the operation of these components. In some examples, control circuitry 245 may be configured to provide timing control signals to coordinate their operation. For example, light drive circuitry 240 may generate one or more light drive signals, which may be used to turn on and off light source 260, based on the timing control signals provided by control circuitry 245. Front-end processing circuitry 216 may use the timing control signals to operate synchronously with light drive circuitry 240. For example, front-end processing circuitry 216 may synchronize the operation of an analog-to-digital converter and a demultiplexer with the light drive signal based on the timing control signals. In addition, the back-end processing circuitry 214 may use the timing control signals to coordinate its operation with front-end processing circuitry 216.

Light drive circuitry 240, as discussed above, may be configured to generate a light drive signal that is provided to light source 260 of sensing device 250. The light drive signal may, for example, control the intensity of light source 260 and the timing of when light source 260 is turned on and off. In some examples, light drive circuitry 240 provides one or more light drive signals to light source 260. Where light source 260 is configured to emit two or more wavelengths of light, the light drive signal may be configured to control the operation of each wavelength of light. The light drive signal may comprise a single signal or may comprise multiple signals (e.g., one signal for each wavelength of light).

Front-end processing circuitry 216 may perform any suitable analog conditioning of the detector signals. The conditioning performed may include any type of filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof. The conditioned analog signals may be processed by an analog-to-digital converter of circuitry 216, which may convert the conditioned analog signals into digital signals. Front-end processing circuitry 216 may operate on the analog or digital form of the detector signals to separate out different components of the signals. Front-end processing circuitry 216 may also perform any suitable digital conditioning of the detector signals, such as low pass, high pass, band pass, notch, averaging, or any other suitable filtering, amplifying, performing an operation on the signal, performing any other suitable digital conditioning, or any combination thereof. Front-end processing circuitry 216 may decrease the number of samples in the digital detector signals. In some examples, front-end processing circuitry 216 may also remove dark or ambient contributions to the received signal.

Back-end processing circuitry 214 may include processing circuitry 210 and memory 220. Processing circuitry 210 may include an assembly of analog or digital electronic components and may be configured to execute software, which may include an operating system and one or more applications, as part of performing the functions described herein with respect to, e.g., processing circuitry 110 of FIG. 1. Processing circuitry 210 may receive and further process physiological signals received from front-end processing circuitry 216. For example, processing circuitry 210 may determine one or more physiological parameter values based on the received physiological signals. For example, processing circuitry 210 may compute one or more of regional oxygen saturation, blood oxygen saturation (e.g., arterial, venous, or both), pulse rate, respiration rate, respiration effort, blood pressure, hemoglobin concentration (e.g., oxygenated, deoxygenated, and/or total), any other suitable physiological parameters, or any combination thereof.

Processing circuitry 210 may perform any suitable signal processing of a signal, such as any suitable band-pass filtering, adaptive filtering, closed-loop filtering, any other suitable filtering, and/or any combination thereof. Processing circuitry 210 may also receive input signals from additional sources not shown. For example, processing circuitry 210 may receive an input signal containing information about treatments provided to the subject from user interface 230. Additional input signals may be used by processing circuitry 210 in any of the determinations or operations it performs in accordance with back-end processing circuitry 214 or regional oximetry device 200.

Processing circuitry 210 is an example of processing circuitry 110 and is configured to perform the techniques of this disclosure. For example, voltage measuring circuitry (e.g., within sensing device 250, light drive circuitry 240, front end processing circuitry 216, back end processing circuitry 214, and/or processing circuitry 210) may be configured to measure a first diode voltage at a light emitting diode (e.g., a red diode, an infrared diode, etc.) of light source 260 while applying a first current through the light emitting diode. Similarly, the voltage measuring circuitry may measure a second diode voltage at the light emitting diode while applying a second current through the light emitting diode and measure a third diode voltage at the light emitting diode while applying a third current through the light emitting diode. For example, processing circuitry 210 may apply, with light drive circuitry 240, the first current at a first magnitude of current, apply the second current at a second magnitude of current that corresponds to the first magnitude of current multiplied by a multiplication factor (e.g., 2, 3, 4, etc.) and apply the third current at a third magnitude of current that corresponds to the second magnitude of current multiplied by the multiplication factor.

Processing circuitry 210 may determine a series resistance for the light emitting diode based on the first diode voltage, the second diode voltage, and the third diode voltage. In some examples, processing circuitry 210 may determine the series resistance based on the first diode voltage, the second diode voltage, the third diode voltage, and the magnitude of the first current. For example, processing circuitry 210 may subtract the second diode voltage from the first diode voltage to determine a first diode difference value, subtract the third diode voltage from the second diode voltage to determine a second diode difference value, and divide a result of subtracting the first diode difference value from the second diode difference value by a magnitude of the first current to generate the series resistance for the light emitting diode.

Processing circuitry 210 may be configured to verify (e.g., validate) that sensing device 250 conforms to the stored calibration information (e.g., are within the range defined by the calibration information) stored in memory 220. For example, processing circuitry 210 may determine that a light emitting diode of light source 260 is valid in response to determining that the estimated series resistance for the light emitting diode corresponds to (e.g., matches, is within a predetermined threshold, etc.) the calibrated series resistance for calibration information for the light emitting diode that was determined (e.g., measured or calculated) during calibration and stored in memory 220. In some examples, processing circuitry 210 may determine that a photodiode of detector 262 is valid in response to determining that the estimated series resistance for the photodiode corresponds to (e.g., matches, is within a predetermined threshold, etc.) the calibrated series resistance for calibration information for the photodiode that was determined (e.g., measured or calculated) during calibration and stored in memory 220.

Processing circuitry 210 may determine that a light emitting diode of light source 260 is valid in response to determining that a forward voltage for the light emitting diode corresponds to (e.g., matches, is within a predetermined threshold, etc.) the calibrated forward voltage for calibration information for the light emitting diode that was determined (e.g., measured or calculated) during calibration and stored in memory 220. In some examples, processing circuitry 210 may determine that a photodiode of detector 262 is valid in response to determining that a forward voltage for the photodiode corresponds to (e.g., matches, is within a predetermined threshold, etc.) the calibrated forward voltage for calibration information for the photodiode that was determined (e.g., measured or calculated) during calibration and stored in memory 220.

Processing circuitry 210 may determine that light source 260 and/or detector 262 are valid based on a combination of forward voltage and series resistance. For example, processing circuitry 210 may determine that a light emitting diode of light source 260 is valid in response to determining that a forward voltage and a series resistance for the light emitting diode correspond to (e.g., match, is within a predetermined threshold, etc.) the calibrated forward voltage and series resistance, respectively, for calibration information for the light emitting diode that was determined (e.g., measured or calculated) during calibration and stored in memory 220. In some examples, processing circuitry 210 may determine that a photodiode of detector 262 is valid in response to determining that a forward voltage and a series resistance for the photodiode correspond to (e.g., match, is within a predetermined threshold, etc.) the calibrated forward voltage and series resistance, respectively, for calibration information for the photodiode that was determined (e.g., measured or calculated) during calibration and stored in memory 220.

Processing circuitry 210 may decrypt calibration information stored in memory 220. For example, processing circuitry 210 may encrypt the calibration information stored in memory 220 using a forward voltage and/or series resistance as an encryption key. As such, processing circuitry 210 may decrypt the encrypted calibration information using the forward voltage and/or series resistance as a key. In this way, processing circuitry 210 may help to ensure that calibration information stored in memory 220 is used with a sensor device conforming with the calibration information.

Processing circuitry 210 may be configured to determine an oxygen saturation level using the light emitting diode of light source 260 and/or the photodiode of detector 262 in response to the determination that sensing device 250 is valid. For example, processing circuitry 210 may determine an intensity of a received photonic signal corresponding to an output photonic signal output using a light emitting diode of light source 260 and a photodiode of detector 262. For example, processing circuitry 210 may drive the light emitting diode to output the output photonic signal towards a subject's tissue and receive, from the photodiode, the received photonic signal after the output photonic signal transmits through the subject's tissue.

Processing circuitry 210 may determine an oxygen saturation level based on the intensity of the received photonic signal and the series resistance. For example, processing circuitry 210 may determine a temperature at the light emitting diode based on the series resistance, the first diode voltage, and the second diode voltage. More specifically, processing circuitry 210 may subtract the second diode voltage from the first diode voltage to determine a first diode difference value, subtract a result of multiplying a magnitude of the first current and the series resistance from the first diode difference value to generate a voltage value for the light emitting diode, and multiply the voltage value for the light emitting diode and a factor parameter value for the light emitting diode to determine the temperature at the light emitting diode.

Processing circuitry 210 may estimate a wavelength for a output photonic signal based on the temperature at the light emitting diode. For example, processing circuitry 210 may determine the oxygen saturation level based on the estimated wavelength for the output photonic signal and the intensity of the received photonic signal and the series resistance.

Processing circuitry 210 may output an indication of the oxygen saturation level. For example, processing circuitry 210 may store an indication of the oxygen saturation level (e.g., a numerical value indicating the oxygen saturation level) for storage at memory 220. Processing circuitry 210 may output an indication of the oxygen saturation level (e.g., a numerical value indicating the oxygen saturation level) to user interface 230 for output on display 232. Processing circuitry 210 may output an indication of the oxygen saturation level (e.g., a numerical value indicating the oxygen saturation level) to communication interface 290 for storage and/or output at one or more external or implanted devices.

Memory 220 may include any suitable computer-readable media capable of storing information that can be interpreted by processing circuitry 210. In some examples, memory 220 may store reference absorption curves, reference sets, determined values, such as blood oxygen saturation, pulse rate, blood pressure, fiducial point locations or characteristics, initialization parameters, any other determined values, or any combination thereof, in a memory device for later retrieval. Memory 220 may also store thresholds for detecting abrupt changes in blood pressure, and so on. Back-end processing circuitry 214 may be communicatively coupled with user interface 230 and communication interface 290.

Memory 220 may store a calibrated forward voltage and/or a calibrated series resistance for one or more light emitting diodes of light source 260. For example, during a calibration of sensing device 250, device 200 (e.g., one or more of light drive circuitry 240, front end processing circuitry 216, back end processing circuitry 214, etc.) may generate the calibrated forward voltage and/or the calibrated series resistance for light emitting diodes of light source 260. For instance, device 200 may determine, during calibration of sensing device 250, a calibrated forward voltage and/or a calibrated series resistance using techniques described herein (e.g., using EQUATIONS 17 and 24).

Memory 220 may store a calibrated forward voltage and/or a calibrated series resistance for one or more photodiodes of detector 262 and/or detector 263. For example, during a calibration of sensing device 250, device 200 (e.g., one or more of light drive circuitry 240, front end processing circuitry 216, back end processing circuitry 214, etc.) may generate the calibrated forward voltage and/or the calibrated series resistance for a photodiode of detector 262. For instance, device 200 may determine, during calibration of sensing device 250, a calibrated forward voltage and/or a calibrated series resistance using techniques described herein (e.g., using EQUATIONS 17 and 24).

During calibration of sensing device 250, device 200 or another device (e.g., a calibration device) may generate calibration information. For example, device 200 or a calibration device may generate an indication of a first wavelength output by a first light emitting diode of light source 260 and an indication of a second wavelength output by a second light emitting diode of light source 260. Memory 220 may store the calibration information based on the indication of a first wavelength output by a first light emitting diode of light source 260 and an indication of a second wavelength output by a second light emitting diode of light source 260. In some examples, device 200 may encrypt the calibration information. As used herein, calibration information may include information for accounting for manufacturing tolerances of light source 260, such as, for example, but not limited to, a wavelength output by light emitting diodes of light source 260. For example, device 200 may encrypt the calibration information based on the calibrated difference of forward voltage. For instance, device 200 may encrypt the calibration information using the calibrated forward voltage and/or the calibrated series resistance of a light emitting diode and/or photodiode as an encryption key. In this way, device 200 may be configured to help to ensure proper construction and/or accuracy of sensing device 250.

User interface 230 may include input device 234, display 232, and speaker 236 in some examples. User interface 230 is an example of user interface 130 shown in FIG. 1, and display 232 is an example of display 132 shown in FIG. 1. User interface 230 may include, for example, any suitable device such as one or more medical devices (e.g., a medical monitor that displays various physiological parameters, a medical alarm, or any other suitable medical device that either displays physiological parameters or uses the output of back-end processing 214 as an input), one or more display devices (e.g., monitor, personal digital assistant (PDA), mobile phone, tablet computer, clinician workstation, any other suitable display device, or any combination thereof), one or more audio devices, one or more memory devices, one or more printing devices, any other suitable output device, or any combination thereof.

Input device 234 may include one or more of any type of user input device such as a keyboard, a mouse, a touch screen, buttons, switches, a microphone, a joystick, a touch pad, or any other suitable input device or combination of input devices. In other examples, input device 234 may be a pressure-sensitive or presence-sensitive display that is included as part of display 232. Input device 234 may also receive inputs to select a model number of sensing device 250, blood pressure sensor 250 (FIG. 2), or blood pressure processing equipment. In some examples, processing circuitry 210 may determine the type of presentation for display 232 based on user inputs received by input device 234.

Figure 3:
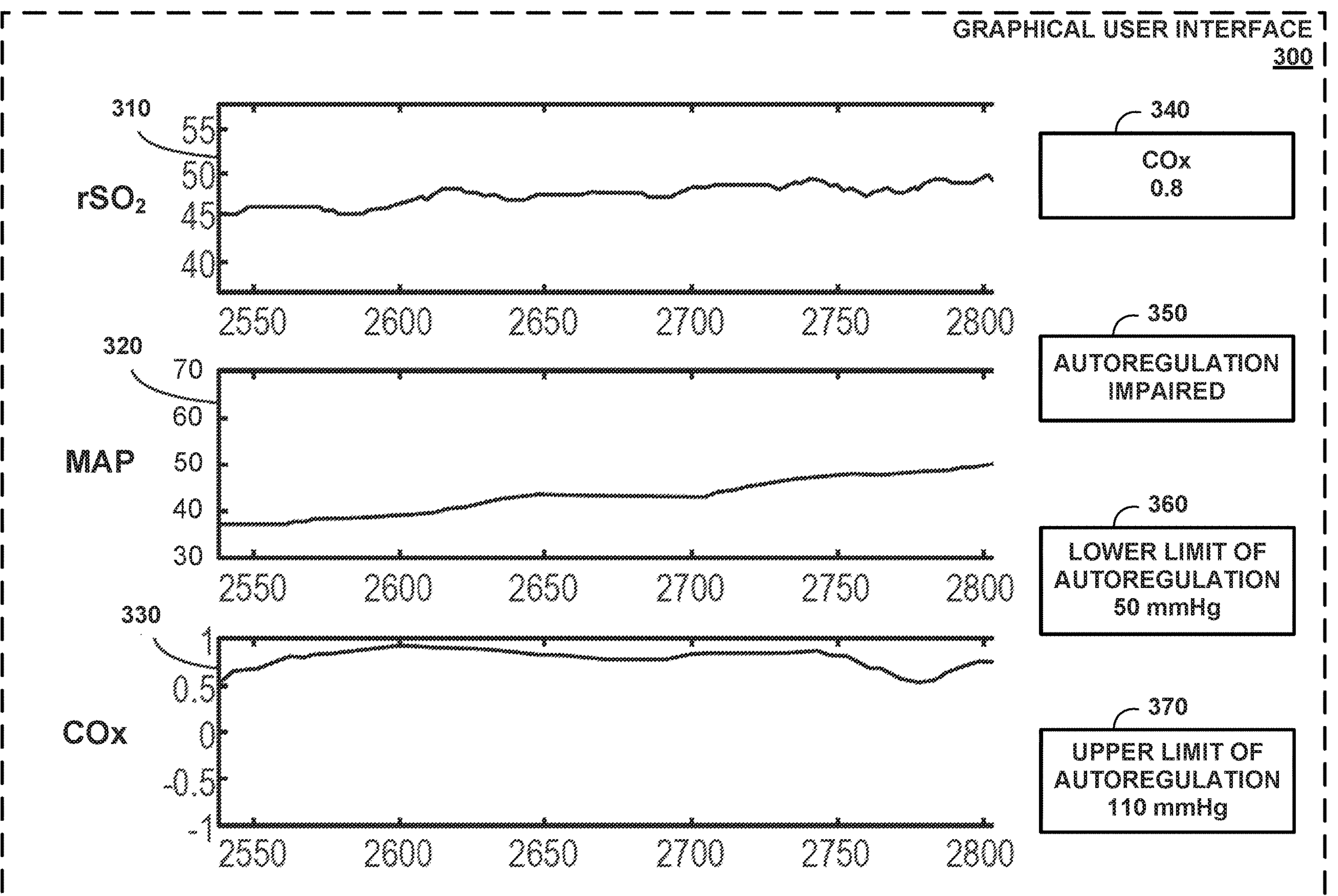
FIG. 3 is a conceptual diagram illustrating an example graphical user interface including autoregulation information presented on a display.

In some examples, the subject may be a medical patient and display 232 may exhibit a list of values which may generally apply to the subject, such as, for example, an oxygen saturation signal indicator, a blood pressure signal indicator, a COx signal indicator, a COx value indicator, and/or an autoregulation status indicator. Display 232 may also be configured to present additional physiological parameter information. Graphical user interface 300 shown in FIG. 3 is an example of an interface that can be presented via display 232 of FIG. 2 under the control of processing circuitry 210. Additionally, display 232 may present, for example, one or more estimates of a subject's regional oxygen saturation generated by regional oximetry device 200 (referred to as an "rSO2" measurement). Display 232 may also present indications of the upper and lower limits of cerebral autoregulation. In some examples, user interface 230 includes speaker 236 that is configured to generate and provide an audible sound that may be used in various examples, such as for example, sounding an audible notification in the event that a patient's physiological parameters are not within a predefined normal range and/or in the event that processing circuitry 210 determines that sensed blood pressure values may be inaccurate due to a non-physiological reason such as due to movement of a blood pressure probe of blood pressure sensor device 151 (FIG. 1).

Communication interface 290 may enable regional oximetry device 200 to exchange information with other external or implanted devices. Communication interface 290 may include any suitable hardware, software, or both, which may allow regional oximetry device 200 to communicate with electronic circuitry, a device, a network, a server or other workstations, a display, or any combination thereof. For example, regional oximetry device 200 may receive MAP (or other measured blood pressure) values and/or oxygen saturation values from an external device via communication interface 290.

The components of regional oximetry device 200 that are shown and described as separate components are shown and described as such for illustrative purposes only. In some examples the functionality of some of the components may be combined in a single component. For example, the functionality of front end processing circuitry 216 and back-end processing circuitry 214 may be combined in a single processor system. Additionally, in some examples the functionality of some of the components of regional oximetry device 200 shown and described herein may be divided over multiple components. For example, some or all of the functionality of control circuitry 245 may be performed in front end processing circuitry 216, in back-end processing circuitry 214, or both. In other examples, the functionality of one or more of the components may be performed in a different order or may not be required. In some examples, all of the components of regional oximetry device 200 can be realized in processor circuitry.

In the above examples, processing circuitry 210, light drive circuitry 240, front end processing circuitry 216, and voltage measuring circuitry are described as performing the example techniques, wherein light drive circuitry 240, front end processing circuitry 216, and voltage measuring circuitry may be part of processing circuitry 210). However, any one or combination of processing circuitry 210, light drive circuitry 240, front end processing circuitry 216, and voltage measuring circuitry may be configured to perform the example techniques. For instance, the example techniques may be performed by circuitry, and example of the circuitry includes any one or any combination of processing circuitry 210, light drive circuitry 240, front end processing circuitry 216, and voltage measuring circuitry.

Figure 4:
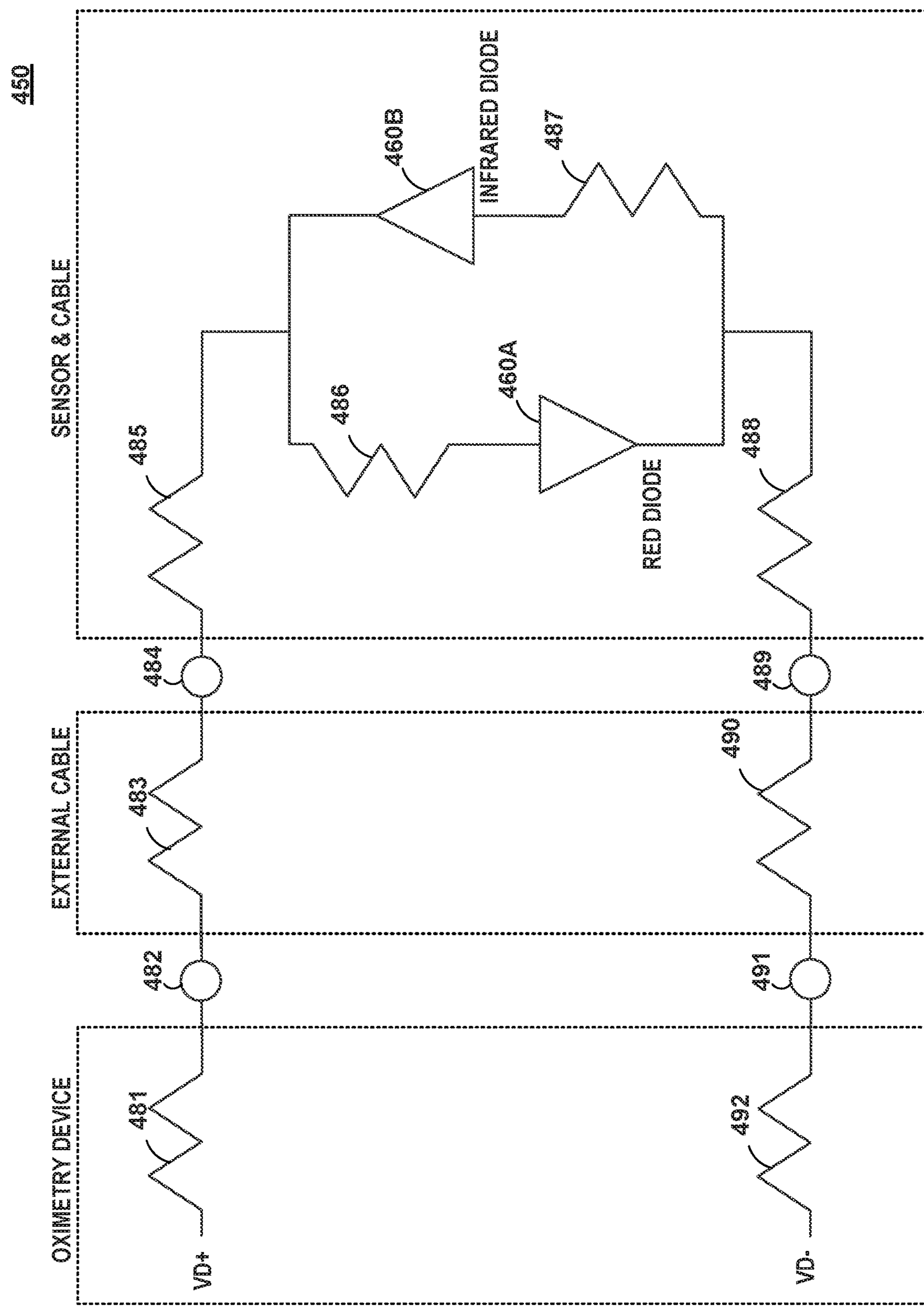
FIG. 4 is a conceptual diagram illustrating an example a resistance for light emitting didoes of a first sensor device, in accordance with techniques described herein.
Figure 5:
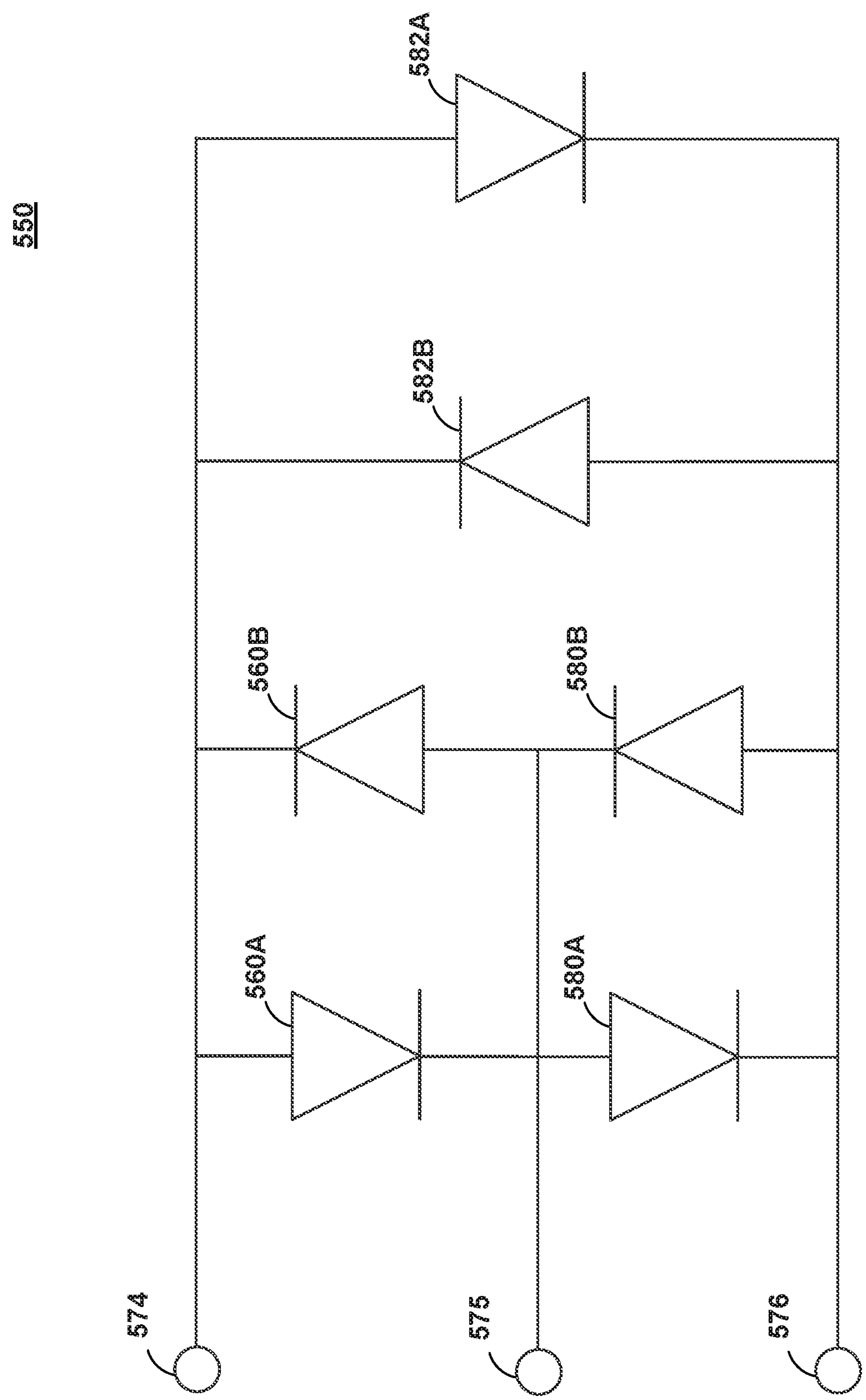
FIG. 5 is a conceptual diagram illustrating an example second sensor device, in accordance with techniques described herein.

FIG. 3 illustrates an example graphical user interface 300 including autoregulation information presented on a display. FIG. 3 is an example of a presentation by processing circuitry 110 on display 132 shown in FIG. 1 or by processing circuitry 210 on display 232 shown in FIG. 2. Although FIGS. 3-5 are described with respect to processing circuitry 110 of regional oximetry device 100 (FIG. 1), in other examples, processing circuitry 210,214, and/or 216 (FIG. 2), alone or in combination with processing circuitry 110, may perform any part of the techniques of FIGS. 3-5.

Graphical user interface 300 may be configured to display various information related to blood pressure, oxygen saturation, the COx index, limits of cerebral autoregulation, and/or cerebral autoregulation status. As shown, graphical user interface 300 may include oxygen saturation signal indicator 310, blood pressure signal indicator 320, and COx signal indicator 330. Graphical user interface 300 may include COx value indicator 340, autoregulation status indicator 350, and limit of autoregulation indicators 360 and 370.

Blood pressure signal indicator 320 may present a set of MAP values determined by processing circuitry 110 of regional oximetry device 100. The MAP values may be based on measured blood pressure values, but the raw measured blood pressure values (e.g., showing intra-cardia cycle variations) may be displayed in other examples. In some examples, blood pressure signal indicator 320 may present MAP values as discrete points over time or in a table. Blood pressure signal indicator 320 may also present MAP values as a moving average or waveform of discrete points. Blood pressure signal indicator 320 may present MAP values as a single value (e.g., a number) representing a current MAP value. Oxygen saturation signal indicator 310 and COx signal indicator 330 may also present rSO2 values and COx values, respectively, as discrete points, in a table, as a moving average, as a waveform, and/or as a single value. In other examples, the data from two or more of oxygen saturation signal indicator 310, blood pressure signal indicator 320, or COx signal indicator 330 may be combined together on a single graph.

COx signal indicator 330 may present a set of correlation coefficients determined by processing circuitry 110. Processing circuitry 110 may determine the correlation coefficients as a function of the oxygen saturation values presented in oxygen saturation signal indicator 310 and the MAP values presented in blood pressure signal indicator 320. In some examples, a COx value at or near one indicates the cerebral autoregulation status of a patient is impaired, as shown in autoregulation status indicator 350.

COx value indicator 340 shows a COx value determined by processing circuitry 110, which is shown as 0.8 in the example of FIG. 3 and may change over time. The COx value of 0.8 may result in a determination by processing circuitry 110 that the cerebral autoregulation status of the patient is impaired. Processing circuitry 110 may be configured to present, as the COx value in COx value indicator 340, the most recently determined COx value. In order to determine the cerebral autoregulation status of a patient for presentation in autoregulation status indicator 350, processing circuitry 110 may determine whether the most recent MAP value shown in blood pressure signal indicator 320 is between the limits of cerebral autoregulation presented in limit of autoregulation indicators 360 and 370. Processing circuitry 110 can present text such as "intact" or "impaired" in autoregulation status indicator 350. Processing circuitry 110 can also present a color such as green (e.g., for intact cerebral autoregulation) or red (e.g., for impaired cerebral autoregulation) to help aid a user's understanding of an autoregulation status of the patient.

In some examples, processing circuitry 110 may present limit of autoregulation indicators 360 and/or 370 in terms of blood pressure, for example, millimeters of mercury (mmHg). Processing circuitry 110 can determine the limits of cerebral autoregulation (LLA and ULA) for presentation in indicators 360 and 370 based on a relationship between the blood pressure of a patient and another physiological parameter of the patient. For example, indicator 360 may be highlighted when the LLA has been exceeded or indicator 360 may be highlighted when the ULA has been exceeded. In other examples, a single indicator may present the type of limit that has been exceed by the MAP value. If the LLA or ULA change, processing circuitry 110 may control user interface 300 to change the value of the LLA or ULA in accordance with any change to that respective value.

In some examples, processing circuitry 110 determines the cerebral autoregulation status for presentation in autoregulation status indicator 350 by comparing the most recently determined MAP value to the limits of cerebral autoregulation. For example, if processing circuitry 110 estimates the LLA at 50 mmHg and determines a MAP value at 40 mmHg, then processing circuitry 110 may determine that the cerebral autoregulation status of the patient is impaired, or not intact. In response to determining that the MAP value is less than or equal to the estimate of the LLA for more than the predetermined period of time, processing circuitry 110 may output a notification in autoregulation status indicator 350 as text, color, blinking, and/or any other suitable visible or audible manner.

FIG. 4 illustrates an example a sensor device 450, in accordance with techniques described herein. The sensor device 450 may be an example of sensor device 150 of FIG. 1 and/or sensing device 250 of FIG. 2. Light emitting diode 460A and light emitting diode 460B (collectively, "light emitting diodes") may form an example of light source 260. Although FIG. 4 is described with respect to regional oximetry device 100 (FIG. 1), in other examples, other devices may perform any part of the technique of FIG. 4. For example, processing circuitry 210, 214, and/or 216 (FIG. 2), alone or in combination with processing circuitry 110, may perform any part of the technique of FIG. 4. In some examples, light emitting diodes 460 may include laser diodes, vertical-cavity surface-emitting lasers, or another device that emits light. In some examples, light emitting diodes 460 may additionally, or alternatively, include photodiodes or another device that detects light (e.g., red light, infrared light, etc.).

In the example of FIG. 4, light emitting diode 460A may be configured to emit red light and light emitting diode 460B may be configured to emit infrared light. In some examples, however, light emitting diode 460A may be configured to emit infrared light and light emitting diode 460B may be configured to emit red light. Moreover, light emitting diodes 460 may be configured to emit light at wavelengths other than red and infrared. In the example of FIG. 4, light emitting diodes 460 are arranged in an anti-parallel configuration. For instance, the anode of light emitting diode 460B may be coupled to the cathode of light emitting diode 460A and the cathode of light emitting diode 460B may be coupled to the anode of light emitting diode 460A.

Each one of light emitting diodes 460 may have a respective body resistance. For example, light emitting diode 460A may include body resistance 486. Light emitting diode 460B may include body resistance 487. Body resistance 486 may correspond to (e.g., be equal to) body resistance 487. In some examples, body resistance 486 may be different from body resistance 487.

Processing circuitry 110 may apply a first current from a first terminal (e.g., VD+) through a first cable (e.g., an external cable and a cable, a cable only, etc.) to an anode of light emitting diode 460A and from a cathode of light emitting diode 460A through a second cable (e.g., an external cable and a cable, a cable only, etc.) to a second terminal (e.g., VD−). In this example, processing circuitry 110 may be configured to measure voltage across the first terminal (e.g., VD+) and the second terminal (e.g., VD−) while applying the first current. Similarly, processing circuitry 110 may apply a second current from the first terminal (e.g., VD+) through the first cable to the anode and from the cathode through the second cable to the second terminal (e.g., VD−). In this example, processing circuitry 110 may be configured to measure voltage across the first terminal (e.g., VD+) and the second terminal (e.g., VD−) while applying the second current. In some examples, processing circuitry 110 may be configured to apply the third current from the first terminal (e.g., VD+) through the first cable to the anode and from the cathode through the second cable to the second terminal (e.g., VD−). In this example, processing circuitry 110 may be configured to measure voltage across the first terminal (e.g., VD+) and the second terminal (e.g., VD−) while applying the third current. The first current, second current, and third current may be ratiometric. For instance, the second current may have a magnitude that is a multiplication factor (e.g., 2, 3, 4, etc.) times larger than the first current and the third current may the multiplication factor times larger than the second current. In this way, a difference between the first current and the second current and/or a difference between the second current and the third current may result in a "constant" forward voltage at the light emitting diode because of how a forward voltage at the diode changes in response to the doubling, tripling, quadrupling, etc. of current at the light emitting diode (e.g., see EQUATION 8).

FIG. 4 illustrates various examples of resistance that an oximeter may account for using techniques described herein. For example, a series resistance for connecting light emitting diode 460A to terminals VD+ and VD− of an oximeter (e.g., regional oximetry device 150, regional oximetry device 250, etc.) may include trace resistance 481, external cable resistance 483 (e.g., a DOC-10 CABLE), cable resistance 485, body resistance 486, cable resistance 488, external cable resistance 490, and trace resistance 492. Additionally, each one of connectors 482, 484, 489, and 491 may include a respective resistance. Similarly, a series resistance for connecting light emitting diode 460B to terminals VD+ and VD− of an oximeter (e.g., regional oximetry device 150, regional oximetry device 250, etc.) may include trace resistance 492, external cable resistance 490 (e.g., a DOC-10 CABLE), cable resistance 488, body resistance 487, cable resistance 485, external cable resistance 483, and trace resistance 481. While the example of FIG. 4 includes 2 light emitting diodes, examples may include more than 2 diodes (e.g., 4 diodes, 6 diodes, 8 diodes, 10 diodes, etc.).

Series resistance for connecting light emitting diodes 460 between terminals VD+ and VD−, which may represent an ohmic resistance between sensor device 450 and a device (e.g., regional oximetry device 150, regional oximetry device 250, etc.) can have several ohms of resistance which can bias the diode voltage reading of light emitting diodes 460. For example, an equivalent circuit may represent light emitting diode 460A with a series resistance that includes a summation of trace resistance 481, external cable resistance 483 (e.g., a DOC-10 CABLE), cable resistance 485, body resistance 486, cable resistance 488, external cable resistance 490, and trace resistance 492. Similarly, an equivalent circuit may represent light emitting diode 460B with a series resistance that includes trace resistance 492, external cable resistance 490 (e.g., a DOC-10 CABLE), cable resistance 488, body resistance 487, cable resistance 485, external cable resistance 483, and trace resistance 481. An oximetry device may be configured to increase accuracy of the measurement by using a very small current to help to reduce the voltage error generated from the series cable resistance.

In accordance with the techniques of the disclosure, a device (e.g., regional oximetry device 150, regional oximetry device 250, etc.) may be configured to use electrical properties of light emitting diodes to effectively account for a forward voltage at light emitting diodes 260, which may allow the device to determine the series resistance. Details of the electrical properties of light emitting diodes are as follows. The device may define electrical current through a diode using EQUATION 1, which may be also referred to as "Shockley's diode equation."

$$I = I_s * \left(\frac{V_J}{e^{nV_T}} - 1\right) \quad \text{EQUATION 1}$$

Where I is the electrical current through a diode (e.g., light emitting diodes 460), $I_s$ is a diffusion current (e.g., device dependent constant), $V_J$ is a voltage applied across the diode, n is the ideality constant, and $V_T$ is defined by EQUATION 2.

$$V_T = \frac{k * T}{q} \quad \text{EQUATION 2}$$

Where k is Boltzman constant (e.g., 1.38E-23 Joules/Kelvin), T is the absolute temperature at the diode in Kelvin, and q is the electron charge (e.g., 1.6E-19 Coulombs).

Shockley's diode equation shown in EQUATION 1 may be approximated as shown in EQUATION 3.

$$I = I_s * \left(\frac{V_D}{e^{nV_T}}\right) \quad \text{EQUATION 3}$$

Solving EQUATION 3 for the junction voltage (e.g., $V_J$) results in EQUATION 4.

$$V_J[I] = nV_T \ln\left(\frac{I}{I_S}\right) \quad \text{EQUATION 4}$$

Adding the series resistance to EQUATION 4 results in EQUATION 5.

$$V_D[I]=V_J[I]+(I*R_{Ser}) \quad \text{EQUATION 5}$$

where $V_D$ is the diode voltage (e.g., at terminals VD+ and VD−), $V_J[I]$ is the junction voltage at a current through the diode, I is the current through the diode, $R_{ser}$ is the series resistance for the diode.

The difference in forward voltage (e.g., $V_J$) of one diode at two different (but ratiometric) current levels may be represented, using EQUATION 4, as shown in EQUATION 6.

$$\Delta V_J[2I - I] = nV_T \ln\left(\frac{2I}{I_S}\right) - nV_T \ln\left(\frac{I}{I_S}\right) \quad \text{EQUATION 6}$$

While the example shown in EQUATIONS 6-24 use a ratio of 2 to 1, other ratios may be used. EQUATIONS 7 and 8 show that a difference of forward voltage at the diode is constant for ratiometric currents.

$$\Delta V_J[2I - I] = nV_T\left(\ln\left(\frac{2I}{I_S}\right) - \ln\left(\frac{I}{I_S}\right)\right) = nV_T \ln\left(\frac{2I * I_S}{I_S * I}\right) = nV_T \ln(2) \quad \text{EQUATION 7}$$

$$\Delta V_J[4I - 2I] = nV_T\left(\ln\left(\frac{4I}{I_S}\right) - \ln\left(\frac{2I}{I_S}\right)\right) = nV_T \ln\left(\frac{4I * I_S}{I_S * 2 * I}\right) = nV_T \ln(2) \quad \text{EQUATION 8}$$

$I_S$ may be assumed to be roughly equivalent at the two different currents. $I_S$ is temperature dependent. A device (e.g., regional oximetry device 150, regional oximetry device 250, etc.) may be configured to use pulsed measurements and quick back-to-back measurements to help to eliminate variability of temperature at the diode.

Combining EQUATIONS 7 and 8 results in EQUATION 9.

$$\Delta V_J[4I-2I]=\Delta V_J[2I-I]==nV_T ln(2) \quad \text{EQUATION 9}$$

That is, EQUATION 9 shows that the forward voltage at a diode may remain relatively constant for ratiometric current when temperature remains constant. Techniques described herein may use a difference of diode voltages to effectively "remove" the forward voltage at the diode. As such, a device (e.g., regional oximetry device 150, regional oximetry device 250, etc.) may be configured to determine the series resistance when a forward voltage at a diode is unknown, which is described in further details below.

The diode voltage (e.g., at terminals VD+ and VD−) may be represented by EQUATIONS 10 and 12.

$$\Delta V_D[4I-2I]=(V_J[4I]+(4I*R_{Ser}))-(V_J[2I]+(2I*R_{Ser})) \quad \text{EQUATION 10}$$

EQUATION 10 may be simplified to EQUATION 11.

$$\Delta V_D[4I-2I]=\Delta V_J[4I-2I]+(2I*R_{Ser})) \quad \text{EQUATION 11}$$

$$\Delta V_D[2I-I]=(V_J[2I]+(2I*R_{Ser}))-(V_J[I]+(I*R_{Ser})) \quad \text{EQUATION 12}$$

EQUATION 12 may be simplified to EQUATION 13.

$$\Delta V_D[2I-I]=\Delta V_J[2I-I]+(I*R_{Ser}) \quad \text{EQUATION 13}$$

Using EQUATION 9 and EQUATION 13 results in EQUATION 14.

$$\Delta V_J[4I-2I]=\Delta V_J[2I-I]\Delta V_J[2I-I]=\Delta V_D[2I-I]-(I*R_{Ser}) \quad \text{EQUATION 14}$$

Using EQUATION 11 and EQUATION 13 results in EQUATION 15.

$$\Delta V_D[4I-2I]=(\Delta V_D[2I-I]-(I*R_{Ser}))+(2I*R_{Ser}) \quad \text{EQUATION 15}$$

Simplifying EQUATION 15 results in EQUATION 16.

$$\Delta V_D[4I-2I]=\Delta V_D[2I-I]+(I*R_{Ser}) \quad \text{EQUATION 16}$$

Solving EQUATION 16 for Rser results in EQUATION 17.

$$R_{Ser} = \frac{\Delta V_D[4I - 2I] - \Delta V_D[2I - I]}{I} \quad \text{EQUATION 17}$$

Table I illustrates example results for techniques for determining a series resistance for an infrared light emitting diode that omits an extensional cable (e.g., DOC 10 in accordance with techniques described herein.

TABLE I

RESISTANCE VALUES FOR AN INFRARED LED WITH SENSOR CABLE ONLY

| I | $V_D$ | $\Delta V_D$ | $R_{Ser}$ |
|---|---|---|---|
| 2.5 mA | 1.16757 V | 0.03566 V | 4.376 Ω |
| 5 mA | 1.20323 V | 0.0466 V | |
| 10 mA | 1.24983 V | | |

Specifically, Table I illustrates an example where a device (e.g., regional oximetry device 150, regional oximetry device 250, etc.) is configured to measure a first diode voltage of 1.16757 V at an infrared light emitting diode while applying a first current of 2.5 mA through the infrared light emitting diode, measure a second diode voltage of 1.20323 V at the infrared light emitting diode while applying a second current of 5 mA through the infrared light emitting diode, and measure a third diode voltage of 1.24983 V at the infrared light emitting diode while applying a third current of 10 mA through the infrared light emitting diode. In this example, the device determines a series resistance at the infrared light emitting diode of 4.376Ω.

Table II illustrates example results for techniques for determining a series resistance for a red light emitting diode that omits an extensional cable (e.g., DOC 10.) in accordance with techniques described herein.

TABLE II

RESISTANCE VALUES FOR A RED LED WITH SENSOR CABLE ONLY

| I | $V_D$ | $\Delta V_D$ | $R_{Ser}$ |
|---|---|---|---|
| 2.5 mA | 1.62241 V | 0.02993 V | 3.472 Ω |
| 5 mA | 1.65234 V | 0.03861 V | |
| 10 mA | 1.69095 V | | |

Table III illustrates example results for techniques for determining a series resistance for an infrared light emitting diode that uses an extensional cable (e.g., DOC 10) in accordance with techniques described herein.

TABLE III

RESISTANCE VALUES FOR AN INFRARED LED WITH SENSOR CABLE AND EXTENSION CABLE

| I | $V_D$ | $\Delta V_D$ | $R_{Ser}$ |
|---|---|---|---|
| 2.5 mA | 1.17254 V | 0.04114 V | 6.544 Ω |
| 5 mA | 1.21368 V | 0.0575 V | |
| 10 mA | 1.27118 V | | |

Table IV illustrates example results for techniques for determining a series resistance for an red light emitting diode that uses an extensional cable (e.g., DOC 10) in accordance with techniques described herein.

TABLE IV

RESISTANCE VALUES FOR A RED LED WITH SENSOR CABLE AND EXTENSION CABLE

| I | $V_D$ | $\Delta V_D$ | $R_{Ser}$ |
|---|---|---|---|
| 2.5 mA | 1.62738 V | 0.0354 V | 5.648 Ω |
| 5 mA | 1.66278 V | 0.04952 V | |
| 10 mA | 1.7123 V | | |

Taking a difference in the $R_{ser}$ values from TABLES I and III and from Tables II and IV can result in an estimated resistance values for the extension cable shown in TABLE V.

TABLE V

RESISTANCE VALUES FOR THE EXTENSION CABLE

| DELTA $R_{Ser}$ for RED LED | DELTA $R_{Ser}$ for INFRARED LED |
|---|---|
| 2.168 Ω | 2.176 Ω |

In this example, the resulting resistance values using techniques described herein for the extension cable are very close to a value measured with a calibrated ohm-meter of 2.2 Ohms.

A device (e.g., regional oximetry device 150, regional oximetry device 250, etc.) may be configured to validate sensor device 450 based on a series resistance using techniques described herein. For example, the device may validate sensor device 450 based on a determination that a total series resistance between VD+ and VD− (e.g., determined using EQUATION 17) corresponds to (e.g., matches, is within a predetermined threshold, etc.) a total calibrated series resistance for calibration information for light emitting diode 460A that was determined (e.g., measured or calculated) during calibration. In some examples, the device may validate sensor device 450 based on a determination that body resistance 486 and/or a combination of body resistance 486 or cable resistances 485, 488 corresponds to (e.g., matches, is within a predetermined threshold, etc.) a calibrated body resistance and/or a calibrated combination of body resistance 486 and cable resistances 485, 488 for calibration information for light emitting diode 460A that was determined (e.g., measured or calculated) during calibration.

A device (e.g., regional oximetry device 150, regional oximetry device 250, etc.) may be configured to use a measured series resistance to authenticate or verify an extension cable is of proper construction. For example, an extension cable (e.g., an external cable that comprises external cable resistances 483, 490) may include an external cable memory chip (e.g., memory arranged inside the external cable) configured to store a calibrated external cable resistance value. In this example, the device may be configured to use the calibrated external cable resistance value stored in the cable memory. For example, the device may subtract one or more of trace resistances 481, 492, a connector resistance for one or more of connectors 482, 484, 489, 491, cable resistances 485, 488, and body resistance 486 from a total series resistance determined using techniques described herein (e.g., EQUATION 17) to estimate an external cable resistance value. In this example, the device may validate sensor device 450 based on a determination that the estimated cable resistance corresponds to (e.g., matches, is within a predetermined threshold, etc.) the calibrated external cable resistance value stored in the cable memory. Memory (e.g., memory 220 of FIG. 2) on the oximetry device may store one or more of trace resistances 481, 492, a connector resistance for one or more of connectors 482, 484, 489, 491, one or more of body resistances 486, 487, and/or other resistance values. In some examples, a cable (e.g., a cable that comprises cable resistances 485, 488) may include a cable memory chip (e.g., memory arranged inside the cable) configured to store a calibrated cable resistance value. In this way, the device may determine that one or more of the oximetry device (e.g., using one or more of trace resistances 481, 492), the external cable, the cable, and the sensor device (e.g., light emitting diodes 460) are valid (e.g., of proper construction and/or accuracy). While this example uses light emitting diode 460A, other examples may apply to other light emitting diodes (e.g., light emitting diode 460B), photodiodes, or other devices or combinations thereof.

With the series resistance value, a device (e.g., regional oximetry device 150, regional oximetry device 250, etc.) may be configured to calculate a temperature at a light emitting diode using a diode voltage as follows. Using EQUATIONS 7 and 13 results in EQUATION 18.

$$\Delta V_D[2I-I]=nV_T ln(2)+(I*R_{Ser}) \quad \text{EQUATION 18}$$

Solving EQUATION 18 for $nV_T$ ln(2) results in EQUATION 19.

$$nV_T ln(2)=\Delta V_D[2I-I]-(I*R_{Ser}) \quad \text{EQUATION 19}$$

Using EQUATION 2 and EQUATION 19 to results in EQUATION 20.

$$n\frac{KT}{q}\ln(2) = \Delta V_D[2I - I] - (I * R_{Ser}) \quad \text{EQUATION 20}$$

Solving EQUATION 20 for T results in EQUATION 21.

$$T = \frac{(\Delta V_D[2I - I] - (I * R_{Ser}))q}{n\,K\ln(2)} \quad \text{EQUATION 21}$$

The ideality constant n may be assumed to be equal to a predetermined number (e.g., 1.0). In some examples, n can be measured at manufacturing as stored in memory 220. For instance, n can be measured using EQUATION 22.

$$n = \frac{(\Delta V_D[2I - I] - (I * R_{Ser}))q}{T\,K\ln(2)} \quad \text{EQUATION 22}$$

That is, a device (e.g., regional oximetry device 150, regional oximetry device 250, etc.) may be configured to generate a factor parameter value based on the ideality constant value.

For instance, the device may calculate the factor parameter value as $$\frac{q}{n\,k\ln(2)}.$$

Again, in some cases, the ideality constant value may be a predetermined value (e.g., 1) and/or may be stored in memory 220.

A device (e.g., regional oximetry device 150, regional oximetry device 250, etc.) may be configured to create a small correction to the temperature equation to account for small temperature impacts on the ideality factor or other variables. For example, the device may apply EQUATION 23.

$$T=T_o+\beta(T_o-T_m) \quad \text{EQUATION 23}$$

where T is the resulting temperature with the correction, $T_o$ is a temperature as measured using Equation 21, β is a temperature correction coefficient value, and $T_m$ is a temperature used when measuring an ideality constant during manufacturing.

A device (e.g., regional oximetry device 150, regional oximetry device 250, etc.) may be configured to calculate a forward voltage of a diode (e.g., an infrared LED, a red LED, etc.) based on the series resistance for the diode. For example, the device can calculate EQUATION 24.

$$V_j[I]=V_D[I]-(I*R_{Ser}) \quad \text{EQUATION 24}$$

A device (e.g., regional oximetry device 150, regional oximetry device 250, etc.) may be configured to compensate for temperature dependence of $I_S$. For example, the device may apply linear interpolation using a temperature coefficient as shown in EQUATION 25.

$$V_C=V_A+(V_A*T_{coeff}*(T_A-T_m)) \quad \text{EQUATION 25}$$

where $V_C$ is the corrected forward voltage (what it would be at $T_m$), $V_A$ is the actual junction forward voltage of the diode, measured at the temperature $T_A$, $T_A$ is the actual temperature of the diode, $T_m$ is the temperature used at manufacturing (e.g., measured when measuring the junction voltage), $T_{coeff}$ is the temperature coefficient of the diode (e.g., an average characterization for each type of LED used). The device may be configured to use $V_C$ and compare $V_C$ to the junction voltage measured at manufacturing.

For example, a device (e.g., regional oximetry device 150, regional oximetry device 250, etc.) may be configured to validate sensor device 450 using techniques described herein. In some examples, the device may validate sensor device 450 based on a determination that a forward voltage (e.g., determined using EQUATION 24 and/or EQUATION 25) at light emitting diode 460 corresponds to (e.g., matches, is within a predetermined threshold, etc.) a calibrated forward voltage for calibration information for light emitting diode 460A that was determined (e.g., measured or calculated) during calibration.

With a temperature, series resistance and diode voltages, a device (e.g., regional oximetry device 150, regional oximetry device 250, etc.) may be configured to calculate what the junction voltage (e.g., forward voltage) would be if measured at different temperatures. This may be useful to verify what the forward voltage would be at the temperature used at manufacturing, to verify that this LED is correct, particularly when the sensor device is used in the field at various temperatures.

Additionally, a device (e.g., regional oximetry device 150, regional oximetry device 250, etc.) may be configured to use the temperature to correct for any shifts in wavelength, especially for red light. For an operating temperature range of 0° C. to 40° C., a wavelength of red light could shift a few nm, which may result in SpO2 errors. For example, the device may be configured to calculate EQUATION 26.

$$\lambda_c=\lambda_m+(\lambda_m*\lambda*(T_A-T_m)) \quad \text{EQUATION 26}$$

where $\lambda_c$ is the calculated/estimated wavelength, $\lambda_m$ is the wavelength measured at manufacturing, $\lambda_{coeff}$ is the temperature coefficient of the diode (e.g., an average characterization for each type of LED used), TA is the actual temperature of the diode as measured by the oximeter in the field, $T_m$ is the temperature of the diode at manufacturing when the wavelength was measured.

A device (e.g., regional oximetry device 150, regional oximetry device 250, etc.) may be configured to apply SpO2 compensation. For example, the device may apply corrections for spO2 errors in extreme temperatures based on compensated wavelength. This may be helpful for emergency medical services (EMS) which often work in outdoor environments. For example, an outdoor environment may be excessively hot or cold, which can lead to spO2 errors. With this compensation, the device may mitigate or remove error from environments that deviate from a nominal temperature or temperature range. The device may be configured to compensate using the wavelength change or just a calibration adjustment.

A device (e.g., regional oximetry device 150, regional oximetry device 250, etc.) may be configured to a carefully measured junction voltage to derive the wavelength using the Planck Einstein equation (EQUATION 27). For example, the device may derive the wavelength using one or more of the doping characteristics of the diode (e.g., a red LED, an infrared LED, etc.) and other non-ideal issues.

$$\lambda = \frac{hc}{qV_J} \qquad \text{EQUATION 27}$$

FIG. 5 is a conceptual diagram illustrating an example second sensor device, in accordance with techniques described herein. Sensor device 550 may be an example of sensor device 150 of FIG. 1 and/or sensing device 250 of FIG. 2. Light emitting diode 560A and light emitting diode 560B (collectively, "light emitting diodes 560"), light emitting diode 580A and light emitting diode 580B (collectively, "light emitting diodes 580"), and light emitting diode 582A and light emitting diode 582B (collectively, "light emitting diodes 582") may each form an example of light source 260.

Although FIG. 5 is described with respect to regional oximetry device 100 (FIG. 1), in other examples, other devices may perform any part of the technique of FIG. 5. For example, processing circuitry 210, 214, and/or 216 (FIG. 2), alone or in combination with processing circuitry 110, may perform any part of the technique of FIG. 5. In some examples, light emitting diodes 560, 580, 582 may include laser diodes, vertical-cavity surface-emitting lasers, or another device that emits light. In some examples, light emitting diodes 560, 580, 582 may additionally, or alternatively, include photodiodes or another device that detects light (e.g., red light, infrared light, etc.), or any combination thereof. While the example of FIG. 5 includes 6 light emitting diodes, examples may include fewer diodes (e.g., 1, 2, 3, 4, or 5 light emitting diodes) or more light emitting diodes (e.g., 7, 8, 9, 10 light emitting diodes, etc.).

In the example of FIG. 5, one light emitting diode of each pair of light emitting diodes 560, 580, 582 may be configured to emit red light and one light emitting diode of each pair of light emitting diodes 560, 580, 582 may be configured to emit infrared light. Moreover, one or more of light emitting diodes 560, 580, 582 may be configured to emit light at wavelengths other than red and infrared. In the example of FIG. 5, each pair of light emitting diodes 560, light emitting diodes 580, and light emitting diodes 582 are arranged in an anti-parallel configuration. For instance, the anode of light emitting diode 560B may be coupled to the cathode of light emitting diode 560A, and the cathode of light emitting diode 560B may be coupled to the anode of light emitting diode 560A.

First terminal 574, second terminal 575, and third terminal 576 may each represent a connection to an oximetry device (e.g., oximetry device 100) using one or more cables, extension cables, one or more connectors, one or more wire bonding pads, or other resistive components. Although not shown, sensor device 550 may include resistive loss due to, for example, cable resistance, one or more connectors, one or more wire bonding pads, one or more printed circuit board (PCB) traces, one or more extension cables, and one or more sensor cables, a body resistance of light emitting diodes 560, 580, 582, and/or other resistive loss.

In accordance with the techniques of the disclosure, a device (e.g., regional oximetry device 150, regional oximetry device 250, etc.) may be configured to measure a first diode voltage at a light emitting diode (e.g., any one of diodes 560, 580, 582) while applying a first current through the light emitting diode. Similarly, the voltage measuring circuitry may measure a second diode voltage at the light emitting diode while applying a second current through the light emitting diode and measure a third diode voltage at the light emitting diode while applying a third current through the light emitting diode. For example, the voltage measuring circuitry may apply the first current at a first magnitude of current, apply the second current at a second magnitude of current that corresponds to the first magnitude of current multiplied by a multiplication factor (e.g., 2, 3, 4, etc.) and apply the third current at a third magnitude of current that corresponds to the second magnitude of current multiplied by the multiplication factor. In this way, a difference between the first current and the second current and/or a difference between the second current and the third current may result in a "constant" forward voltage at the light emitting diode because of how a forward voltage at the diode changes in response to the doubling, tripling, quadrupling, etc. of current at the light emitting diode (e.g., see EQUATION 8).

The device (e.g., regional oximetry device 150, regional oximetry device 250, etc.) may be configured to determine a series resistance for the light emitting diode based on the first diode voltage, the second diode voltage, and the third diode voltage. In some examples, processing circuitry 110 may determine the series resistance based on the first diode voltage, the second diode voltage, the third diode voltage, and at least one of the magnitude of the first current, the magnitude of the second current, and the magnitude of the third current. For example, the device may apply EQUATION 17. In this way, techniques described herein may determine a forward voltage at a light emitting diode in a manner that accounts for device specific parameters of the light emitting diode and/or a non-linear forward voltage relationship between forward voltage and current at the light emitting diode.

The device (e.g., regional oximetry device 150, regional oximetry device 250, etc.) may be configured to determine whether sensor device 550 is valid (e.g., based on the series resistance, a forward voltage, etc.) and, in response to determining sensor device 550 is valid (e.g., of proper construction and/or accuracy), determine an oxygen saturation level based on the intensity of the received photonic signal and the series resistance. For example, processing circuitry 110 may determine a temperature at the light emitting diode based on the series resistance, the first diode voltage, and the second diode voltage. For instance, the device may apply EQUATION 21. The device may be configured to estimate a wavelength for a output photonic signal based on the temperature at the light emitting diode. For example, the device may determine the oxygen saturation level based on the estimated wavelength for the output photonic signal and the intensity of the received photonic signal and the series resistance.

Figure 6:
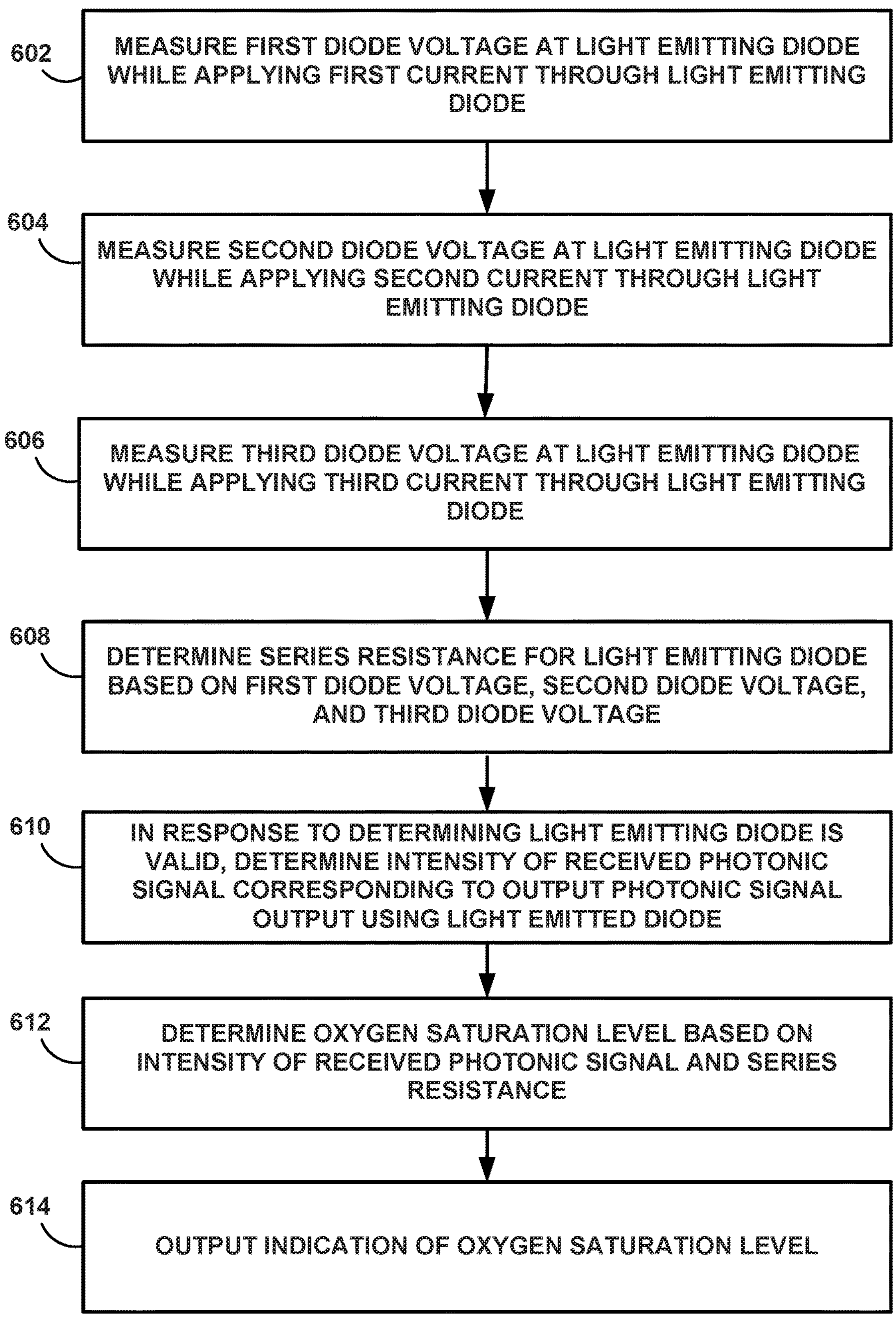
FIG. 6 is a flow diagram illustrating an example technique for measuring oxygen saturation, in accordance with techniques described herein.

FIG. 6 is a flow diagram illustrating an example technique for measuring oxygen saturation, in accordance with techniques described herein. Although FIG. 6 is described with respect to circuitry, such circuitry may include one or more of processing circuitry 110, voltage measuring circuitry (e.g., within sensing device 150, sensing circuitry 140, and/or processing circuitry 110), sensing device 150, sensing circuitry 140, processing circuitry 210, 214, and/or 216 (FIG. 2). While FIG. 6 is described using sensor device 450, the techniques of FIG. 6 may be applied to other sensor devices, such as, for example, sensor device 550 of FIG. 5. In some examples, the first light emitting diode and/or the second light emitting diode may include laser diodes, vertical-cavity surface-emitting lasers, or another device that emits light. In some examples, the first light emitting diode and/or the second light emitting diode may additionally, or alternatively, include photodiodes or another device that detects light (e.g., red light, infrared light, etc.).

In the example of FIG. 6, circuitry may measure a first diode voltage at a light emitting diode while applying a first current through the light emitting diode (602). The circuitry may measure a second diode voltage at the light emitting diode while applying a second current through the light emitting diode (604). The circuitry may measure a third diode voltage at the light emitting diode while applying a third current through the light emitting diode (606).

The circuitry may determine a series resistance for the light emitting diode based on the first diode voltage, the second diode voltage, and the third diode voltage (608). For example, the circuitry may calculate EQUATION 17. The circuitry may, in response to determining the light emitting diode is valid, determine an intensity of a received photonic signal corresponding to an output photonic signal output using the light emitting diode (610). For example, the circuitry may determine that the light emitting diode is valid based on the series resistance. For instance, the circuitry may determine that the light emitting diode is valid (e.g., of proper construction and/or accuracy) based on determining a difference between the series resistance and a calibrated series resistance is less than a first predetermined threshold. In some examples, the circuitry may determine a forward voltage for the light emitting diode based on the series resistance (e.g., using EQUATION 24 and/or EQUATION 25). In this example, the circuitry may determine that the light emitting diode is valid based on determining a difference between the forward voltage and a calibrated forward voltage is less than a second predetermined threshold. In this example, in response to determining the light emitting diode is valid, the circuitry may drive the light emitting diode to output the output photonic signal towards a subject's tissue and receive, from a detector, the received photonic signal after the output photonic signal transmits through the subject's tissue.

The circuitry may determine an oxygen saturation level based on the intensity of the received photonic signal and the series resistance (612). For example, the circuitry may determine a temperature at the light emitting diode using EQUATION 21. Processing circuitry 110 may be configured to use the temperature to correct for any shifts in wavelength using EQUATION 27. The circuitry may output an indication of the oxygen saturation level (614). For example, the circuitry may store an indication of the oxygen saturation level (e.g., a numerical value indicating the oxygen saturation level) for storage at memory 220 and/or output the indication of the oxygen saturation level to user interface 230 for output on display 232.

The following are examples of the description herein.

Example 1. A device for measuring oxygen saturation, the device comprising circuitry configured to: measure a first diode voltage at a light emitting diode while applying a first current through the light emitting diode; measure a second diode voltage at the light emitting diode while applying a second current through the light emitting diode; measure a third diode voltage at the light emitting diode while applying a third current through the light emitting diode; determine a series resistance for the light emitting diode based on the first diode voltage, the second diode voltage, and the third diode voltage; determine an intensity of a received photonic signal corresponding to an output photonic signal output using the light emitting diode; determine an oxygen saturation level based on the intensity of the received photonic signal and the series resistance; and output an indication of the oxygen saturation level.

Example 2. The device of example 1, wherein the circuitry is configured to: determine that the light emitting diode is valid based on the series resistance, wherein the determination of the intensity of the received photonic signal is in response to the determination that the light emitting diode is valid.

Example 3. The device of example 2, wherein the circuitry is configured to: determine a forward voltage for the light emitting diode based on the series resistance, wherein the determination that the light emitting diode is valid is further based on the forward voltage for the light emitting diode.

Example 4. The device of any one of examples 1-3, wherein the circuitry is configured to: apply the first current at a first magnitude of current; apply the second current at a second magnitude of current that corresponds to the first magnitude of current multiplied by a multiplication factor; and apply the third current at a third magnitude of current that corresponds to the second magnitude of current multiplied by the multiplication factor.

Example 5. The any one of examples 1-4, wherein the determination of the oxygen saturation level is further based on at least one of a magnitude of the first current, a magnitude of the second current, or a magnitude of the third current.

Example 6. The device of any one of examples 1-5, wherein, to determine the series resistance, the circuitry is configured: subtract the second diode voltage from the first diode voltage to determine a first diode difference value; subtract the third diode voltage from the second diode voltage to determine a second diode difference value; and divide a result of subtracting the first diode difference value from the second diode difference value by a magnitude of the first current.

Example 7. The device of any one of examples of 1-6, wherein the circuitry is configured to: apply the first current from a first terminal through a first cable to an anode of the light emitting diode and from a cathode of the light emitting diode through a second cable to a second terminal, wherein, to measure the first diode voltage, the circuitry is configured to measure voltage across the first terminal and the second terminal while applying the first current; apply the second current from the first terminal through the first cable to the anode and from the cathode through the second cable to the second terminal, wherein, to measure the second diode voltage, the circuitry is configured to measure voltage across the first terminal and the second terminal while applying the second current; and apply the third current from the first terminal through the first cable to the anode and from the cathode through the second cable to the second terminal, wherein, to measure the third diode voltage, the circuitry is configured to measure voltage across the first terminal and the second terminal while applying the third current.

Example 8. The device of any one of examples 1-7, wherein the circuitry is configured to determine a temperature at the light emitting diode based on the series resistance, the first diode voltage, and the second diode voltage, wherein the determination of the oxygen saturation level is further based on the temperature at the light emitting diode.

Example 9. The device of example 8, wherein, to determine the temperature at the light emitting diode, the circuitry is configured to: subtract the second diode voltage from the first diode voltage to determine a first diode difference value; subtract a result of multiplier a magnitude of the first current and the series resistance from the first diode difference value to generate a voltage value for the light emitting diode; and multiply the voltage value for the light emitting diode and a factor parameter value for the light emitting diode.

Example 10. The device of example 9, further comprising memory configured to store a ideality constant value for the light emitting diode, wherein the circuitry is configured to generate the factor parameter value based on the ideality constant value.

Example 11. The device of example 10, wherein, to generate the factor parameter value, the circuitry is configured to calculate the factor parameter value as: q/n k ln(2), wherein q is a magnitude of charge of an electron, n is the ideality constant value, k is a Boltzmann constant, and ln (2) is a natural logarithm of 2.

Example 12. The device of any one of examples 9-11, wherein the circuitry is configured to: estimate a wavelength for the output photonic signal based on the temperature at the light emitting diode, wherein the determination of the oxygen saturation level is further based on the estimated wavelength for the output photonic signal.

Example 13. The device of any one of examples 1-12, wherein the circuitry is configured to: drive the light emitting diode to output the output photonic signal towards a subject's tissue; and receive, from a detector, the received photonic signal after the output photonic signal transmits through the subject's tissue.

Example 14. The device of any one of examples 1-13, wherein the light emitting diode is configured to emit red light or emit infrared light.

Example 15. The device of example 1-14, wherein the light emitting diode is a first light emitting diode and wherein an anode of a second light emitting diode is coupled to a cathode of the first light emitting diode and a cathode of the second light emitting diode is coupled to an anode of the first light emitting diode.

Example 16. A method for measuring oxygen saturation, the method comprising: measuring, by circuitry, a first diode voltage at a light emitting diode while applying a first current through the light emitting diode; measuring, by the circuitry, a second diode voltage at the light emitting diode while applying a second current through the light emitting diode; measuring, by the circuitry, a third diode voltage at the light emitting diode while applying a third current through the light emitting diode; determining, by the circuitry, a series resistance for the light emitting diode based on the first diode voltage, the second diode voltage, and the third diode voltage; determining, by the circuitry, an intensity of a received photonic signal corresponding to an output photonic signal output using the light emitting diode; determining, by the circuitry, an oxygen saturation level based on the intensity of the received photonic signal and the series resistance; and outputting, by the circuitry, an indication of the oxygen saturation level.

Example 17. The method of example 16, comprising: determining, by the circuitry, that the light emitting diode is valid based on the series resistance, wherein determining the intensity of the received photonic signal is in response to the determination that the light emitting diode is valid.

Example 18. The method of example 17, comprising: determining, by the circuitry, a forward voltage for the light emitting diode based on the series resistance, wherein determining that the light emitting diode is valid is further based on the forward voltage for the light emitting diode.

Example 19. The method of any one of examples 16-18, comprising: applying, by the circuitry, the first current at a first magnitude of current; applying, by the circuitry, the second current at a second magnitude of current that corresponds to the first magnitude of current multiplied by a multiplication factor; and applying, by the circuitry, the third current at a third magnitude of current that corresponds to the second magnitude of current multiplied by the multiplication factor.

Example 20. A system for measuring oxygen saturation, the system comprising: a sensor device comprising a light emitting diode; an oximetry device comprising circuitry configured to: measure a first diode voltage at the light emitting diode while applying a first current through the light emitting diode; measure a second diode voltage at the light emitting diode while applying a second current through the light emitting diode; determine a series resistance for the light emitting diode based on the first diode voltage and the second diode voltage; determine an intensity of a received photonic signal corresponding to an output photonic signal output using the light emitting diode; determine an oxygen saturation level based on the intensity of the received photonic signal and the series resistance; and output an indication of the oxygen saturation level.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to devices 100 and 200, processing circuitry 110, 210, 214, and 216, memories 120 and 220, displays 132 and 232, sensing circuitries 140-142, circuitries 240 and 245, sensing devices 150, 151, 152, and 250, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in patient monitors, such as multiparameter patient monitors (MPMs) or other devices, remote servers, or other devices. The term "processor" or "processing circuitry" may generally refer to any of the foregoing logic circuitry, alone or in combination with other logic circuitry, or any other equivalent circuitry.

As used herein, the term "circuitry" refers to an ASIC, an electronic circuit, a processor (shared, dedicated, or group) and memory that execute one or more software or firmware programs, a combinational logic circuit, or other suitable components that provide the described functionality. The term "processing circuitry" refers one or more processors distributed across one or more devices. For example, "processing circuitry" can include a single processor or multiple processors on a device. "Processing circuitry" can also include processors on multiple devices, wherein the operations described herein may be distributed across the processors and devices.

Such hardware, software, firmware may be implemented within the same device or within separate devices to support the various operations and functions described in this disclosure. For example, any of the techniques or processes described herein may be performed within one device or at least partially distributed amongst two or more devices, such as between devices 100 and 200, processing circuitry 110, 210, 214, and 216, memories 120 and 220, sensing circuitries 140-142, and/or circuitries 240 and 245. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache). Elements of devices and circuitry described herein, including, but not limited to, devices 100 and 200, processing circuitry 110, 210,214, and 216, memories 120 and 220, displays 132 and 232, sensing circuitries 140-142, circuitries 240 and 245, sensing devices 150-152 and 250 may be programmed with various forms of software. The one or more processors may be implemented at least in part as, or include, one or more executable applications, application modules, libraries, classes, methods, objects, routines, subroutines, firmware, and/or embedded code, for example.

Various examples of the disclosure have been described. Any combination of the described systems, operations, or functions is contemplated. These and other examples are within the scope of the following claims.

What is claimed is:

1. A device for measuring oxygen saturation, the device comprising circuitry configured to:

determine a series resistance for a light emitting diode based on a first diode voltage at the light emitting diode for a first current, a second diode voltage at the light emitting diode for a second current, and a third diode voltage at the light emitting diode for a third current;

determine an intensity of a received photonic signal corresponding to an output photonic signal output using the light emitting diode;

determine an oxygen saturation level based on the intensity of the received photonic signal and the series resistance; and output an indication of the oxygen saturation level.

2. The device of claim 1, wherein the circuitry is configured to determine that the light emitting diode is valid based on the series resistance, wherein the determination of the intensity of the received photonic signal is in response to the determination that the light emitting diode is valid.

3. The device of claim 2, wherein the circuitry is configured to determine a forward voltage for the light emitting diode based on the series resistance, wherein the determination that the light emitting diode is valid is further based on the forward voltage for the light emitting diode.

4. The device of claim 1, wherein, to determine the series resistance, the circuitry is configured to:

apply the first current at a first magnitude of current;

apply the second current at a second magnitude of current that corresponds to the first magnitude of current multiplied by a multiplication factor; and apply the third current at a third magnitude of current that corresponds to the second magnitude of current multiplied by the multiplication factor.

5. The device of claim 1, wherein to determine the oxygen saturation level, the circuitry is configured to determine the oxygen saturation level based on the intensity of the received photonic signal and the series resistance and further based on at least one of a magnitude of the first current, a magnitude of the second current, or a magnitude of the third current.

6. The device of claim 1, wherein, to determine the series resistance, the circuitry is configured:

subtract the second diode voltage from the first diode voltage to determine a first diode difference value;

subtract the third diode voltage from the second diode voltage to determine a second diode difference value; and divide a result of subtracting the first diode difference value from the second diode difference value by a magnitude of the first current.

7. The device of claim 1, wherein, to determine the series resistance, the circuitry is configured to:

apply the first current from a first terminal through a first cable to an anode of the light emitting diode and from a cathode of the light emitting diode through a second cable to a second terminal and measure the first diode voltage, wherein, to measure the first diode voltage, the circuitry is configured to measure a voltage across the first terminal and the second terminal while the circuitry applies the first current;

apply the second current from the first terminal through the first cable to the anode and from the cathode through the second cable to the second terminal and measure the second diode voltage, wherein, to measure the second diode voltage, the circuitry is configured to measure a voltage across the first terminal and the second terminal while the circuitry applies the second current; and apply the third current from the first terminal through the first cable to the anode and from the cathode through the second cable to the second terminal and measure the third diode voltage, wherein, to measure the third diode voltage, the circuitry is configured to measure a voltage across the first terminal and the second terminal while the circuitry applies the third current.

8. The device of claim 1, wherein the circuitry is configured to determine a temperature at the light emitting diode based on the series resistance, the first diode voltage, and the second diode voltage, wherein to determine the oxygen saturation level, the circuitry is configured to determine the oxygen saturation level based on the intensity of the received photonic signal and the series resistance and further based on the temperature at the light emitting diode.

9. The device of claim 8, wherein, to determine the temperature at the light emitting diode, the circuitry is configured to:

subtract the second diode voltage from the first diode voltage to determine a first diode difference value;

subtract a result of multiplier a magnitude of the first current and the series resistance from the first diode difference value to generate a voltage value for the light emitting diode; and multiply the voltage value for the light emitting diode and a factor parameter value for the light emitting diode.

10. The device of claim 9, further comprising memory configured to store a ideality constant value for the light emitting diode, wherein the circuitry is configured to generate the factor parameter value based on the ideality constant value.

11. The device of claim 10, wherein, to generate the factor parameter value, the circuitry is configured to calculate the factor parameter value as:

$$\frac{q}{n\,k\ln(2)}$$

wherein q is a magnitude of charge of an electron, n is the ideality constant value, k is a Boltzmann constant, and ln (2) is a natural logarithm of 2.

12. The device of claim 8, wherein the circuitry is configured to estimate a wavelength for the output photonic signal based on the temperature at the light emitting diode, wherein to determine the oxygen saturation level, the circuitry is configured to determine the oxygen saturation level based on the intensity of the received photonic signal and the series resistance, and further based on the estimated wavelength for the output photonic signal.

13. The device of claim 1, wherein the circuitry is configured to:

drive the light emitting diode to output the output photonic signal towards a subject's tissue; and receive, from a detector, the received photonic signal after the output photonic signal transmits through the subject's tissue.

14. The device of claim 1, wherein the light emitting diode is configured to emit red light or emit infrared light.

15. The device of claim 1, wherein the light emitting diode is a first light emitting diode and wherein an anode of a second light emitting diode is coupled to a cathode of the first light emitting diode and a cathode of the second light emitting diode is coupled to an anode of the first light emitting diode.

16. A method for measuring oxygen saturation, the method comprising:

determining, by circuitry, a series resistance for the light emitting diode based on a first diode voltage at the light emitting diode for a first current, a second diode voltage at the light emitting diode for a second current, and a third diode voltage at the light emitting diode for a third current;

determining, by the circuitry, an intensity of a received photonic signal corresponding to an output photonic signal output using the light emitting diode;

determining, by the circuitry, an oxygen saturation level based on the intensity of the received photonic signal and the series resistance; and outputting, by the circuitry, an indication of the oxygen saturation level.

17. The method of claim 16, comprising determining, by the circuitry, that the light emitting diode is valid based on the series resistance, wherein determining the intensity of the received photonic signal is in response to the determination that the light emitting diode is valid.

18. The method of claim 17, comprising determining, by the circuitry, a forward voltage for the light emitting diode based on the series resistance, wherein determining that the light emitting diode is valid is further based on the forward voltage for the light emitting diode.

19. The method of claim 16, wherein determining the series resistance comprises:

applying, by the circuitry, the first current at a first magnitude of current;

applying, by the circuitry, the second current at a second magnitude of current that corresponds to the first magnitude of current multiplied by a multiplication factor; and applying, by the circuitry, the third current at a third magnitude of current that corresponds to the second magnitude of current multiplied by the multiplication factor.

20. A system for measuring oxygen saturation, the system comprising:

a sensor device comprising a light emitting diode; and an oximetry device comprising circuitry configured to:

determine a series resistance for a light emitting diode based on a first diode voltage at the light emitting diode for a first current, a second diode voltage at the light emitting diode for a second current, and a third diode voltage at the light emitting diode for a third current;

determine an intensity of a received photonic signal corresponding to an output photonic signal output using the light emitting diode;

determine an oxygen saturation level based on the intensity of the received photonic signal and the series resistance; and output an indication of the oxygen saturation level.

* * * * *